(12) United States Patent
Ecco et al.

(10) Patent No.: US 12,247,255 B2
(45) Date of Patent: Mar. 11, 2025

(54) CAPTURE PROBES AND USES THEREOF

(71) Applicant: Sophia Genetics S.A., Saint-Sulpice (CH)

(72) Inventors: Gabriela Ecco, Saint-Sulpice (CH); Xiaobin Xing, Saint-Sulpice (CH); Adrian Willig, Saint-Sulpice (CH); Zhenyu Xu, Saint-Sulpice (CH)

(73) Assignee: SOPHIA GENETICS S.A., Rolle (CH)

( * ) Notice: Subject to any disclaimer, the term of this patent is extended or adjusted under 35 U.S.C. 154(b) by 25 days.

(21) Appl. No.: 17/484,928

(22) Filed: Sep. 24, 2021

(65) Prior Publication Data

US 2022/0380843 A1 Dec. 1, 2022

(30) Foreign Application Priority Data

May 20, 2021 (EP) ..................................... 21175123

(51) Int. Cl.
*C12Q 1/6874* (2018.01)
*C12N 15/10* (2006.01)
*C12Q 1/6853* (2018.01)

(52) U.S. Cl.
CPC ....... *C12Q 1/6874* (2013.01); *C12N 15/1068* (2013.01); *C12Q 1/6853* (2013.01)

(58) Field of Classification Search
None
See application file for complete search history.

(56) References Cited

U.S. PATENT DOCUMENTS

| | | |
|---|---|---|
| 2005/0266459 A1 | 12/2005 | Poulsen et al. |
| 2014/0120540 A1 | 5/2014 | Seligmann et al. |
| 2015/0167077 A1 | 6/2015 | Fehr et al. |
| 2015/0322498 A1 | 11/2015 | Takeuchi |

FOREIGN PATENT DOCUMENTS

| | | |
|---|---|---|
| CN | 111321202 A | 6/2020 |
| EP | 3647420 A1 | 5/2020 |

OTHER PUBLICATIONS

Ahern ( "Biochemical, Reagents Kits Offer Scientists Good Return On Investment" The Scientist, vol. 9, Issue 15, published Jul. 24, 1995). http://www.the-scientist.com/article/print/16618/ (Year: 1995).*
European Search Report in European Patent Appl. No. 21175123.5, dated Oct. 27, 2021, 10 pages.
Kohsaka et al., Comprehensive Assay For The Molecular Profiling Of Cancer By Target Enrichment From Formalin-Fixed Paraffin-Embedded Specimens, 2019, Cancer Science, vol. 110, No. 4, pp. 1464-1479.
Heyer et al., Sequencing Strategies for Fusion Gene Detection, 2020, Bioessays. vol. 42, No. 7.
Extended European Search Report of the European Patent Office in related European Patent Appl. No. 24156139.8, dated Jul. 25, 2024, 9 pages.

* cited by examiner

*Primary Examiner* — Nancy J Leith
*Assistant Examiner* — Jessica D Parisi
(74) *Attorney, Agent, or Firm* — Bochner PLLC; Andrew Bochner; Eric Kleinertz

(57) ABSTRACT

The present invention is directed to the probes for detecting known and unknown fusion genes, related methods of detection of fusion genes, uses and kits related thereto. In particular, the invention relates to methods of diagnosing and monitoring of a cancer.

8 Claims, 5 Drawing Sheets

Specification includes a Sequence Listing.

High overlap probe design:

Low overlap probe design:

CAPTURE PROBES AND USES THEREOF

CLAIM OF PRIORITY

This application claims the benefit of E.U. Provisional Application No. EP21175123, the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Nov. 24, 2021, is named 1200_021US_SL.txt and is 22,338 bytes in size.

FIELD OF THE INVENTION

The present invention relates to the field of fusion gene detection and in particular to the probes for detecting gene fusion events, methods of detection of fusion genes, uses and kits related thereto. In particular, the present invention relates to a method of diagnosis and/or monitoring of a cancer.

BACKGROUND

Fusion genes are important clinical biomarkers that guide diagnosis, inform prognosis and support treatment decisions. They originate from chromosomal rearrangements such as translocations, inversions and deletions and can lead to chimeric RNAs and proteins. Fusion genes normally comprise two partners: a primary fusion partner, which can be, for instance, a kinase gene, and a secondary fusion partner.

Fusion genes can be detected by diverse molecular assays such as fluorescence in situ hybridization (FISH), reverse transcription polymerase chain reaction (RT-PCR), immunohistochemistry (IHC) and Next-Generation Sequencing (NGS)-based techniques.

FISH relies on nucleic acid probes containing fluorophores that hybridize to specific nucleic acid sequences allowing visualization by fluorescence microscopy. RT-PCR uses specific sets of primers designed to target and amplify known fusion gene transcripts by PCR. IHC detects fusions with the use of antibodies that specifically bind fusion proteins and detects them by microscopy. While widely used in the clinics, these techniques are characterized by their low throughput and are limited to the detection of fusion events between known partners.

In contrast NGS-based techniques allow comprehensive and parallel detection of multiple gene fusion events across multiple patients. There are a few variations of this technique, each based on different library preparation method. Multiplex PCR (mPCR) is a higher throughput version of RT-PCR, in which pools of gene-specific primers are used to detect different fusion genes, and the PCR product is then converted to an NGS library that is sequenced. This technique has the advantages of being relatively fast but requires both fusion partners to be known. Anchored Multiplex PCR (AMP), which is similar to mPCR but in which gene-specific primers are used in combination with a generic primer partially overcomes this limitation allowing detection of novel fusions events for a given known fusion partner. However, both AMP and mPCR are impacted by the inherent technical limitations of PCR, such as off-target primer binding and primer dimerization, which increases with increasing panel size (*Heyer and Blackburn.* 2020 *Bioessays* 42(7):e2000016).

Currently, alternatives to amplicon or PCR-based techniques are whole genome sequencing (WGS) and RNA sequencing (RNA-seq). These techniques allow unbiased characterization of the full genome or transcriptome (respectively), including known and novel fusions. However, due to the high cost of this type of genome-wide approach these techniques are still seldomly used for clinical applications. Hybridization capture-based NGS provides a cost-effective alternative, in which WGS or RNA-seq libraries are subjected to a target enrichment step before sequencing. This step restricts the regions that will be sequenced, while allowing detection of both known and novel fusion events (Hrdlickova et al., 2017. *Wiley Interdiscip Rev RNA* 2017, 8:e 1364; Heyer and Blackburn, 2020, supra).

Hybridization capture-based NGS is especially interesting for fusion detection using RNA-seq libraries. In this technique, RNA molecules are converted to cDNA, which is then ligated to sequencing adapters and amplified to generate whole transcriptome libraries. These libraries are subjected to hybridization capture using probes, linked to a biochemical moiety (typically biotin), designed to target and isolate the sequences of interest, which are subsequently amplified and sequenced (Mercer et al., 2014. *Nat Protoc.* 9(5):989-1009; Heyer and Blackburn, 2020, supra).

Therefore, an important step for the success of hybridization capture is the probe design. Various examples of probe designs are known, such as those described in EP3647420A1, wherein the probes hybridize to a region derived from either gene A or B of cDNA prepared from the fusion gene transcript comprising a part of gene A on the 5' side and a part of gene B on the 3' side linked to each other at a potential junction point. Accurate probe design guarantees that only the targets of interest will be captured. For the detection of fusion genes this is a particularly challenging task, as the design of probes depends on the fusion partners and breakpoints, which are not always known and vary greatly from one medical application to another. Furthermore, an important limitation of fusion probe design is how to place the probes in order to detect novel and known fusions alike, without capturing too many reads from the wild type (WT) partner genes that may not be of diagnostic interest.

Probes suitable for detection of gene fusion events can either be designed such that they are homologous to the known partner (hereafter primary partner), which would allow the detection of almost any fusion involving that region of the partner (hereafter universal probes). Alternatively, probes can also be design across the breakpoint, overlapping both with primary and secondary fusion partner so that to enrich for known fusions (hereafter specific probes). Designing universal probes is the most common form of probe design, however they are less specific and may require deeper sequencing to detect lowly expressed fusions. Hence, to guarantee the optimal detection of relevant known fusions, the approach is to also design probes that are specific for a particular fusion/breakpoint. This approach, however, requires a careful design balance in order to optimize sequencing reads.

Therefore, there is a need to improve probes and probes sets for the simultaneous capture and detection of known and novel fusion gene partners while limiting capture of WT (wild type) secondary fusion partner counterpart.

SUMMARY

The present invention may be based on the finding that it is possible to optimize the design of probes to detect specific known fusions so that to minimize capturing a WT secondary fusion partner counterpart. This design may allow reduced capture of a WT counterpart of the secondary partner of a specific fusion, allowing the detection of said fusion, while minimizing the generation of sequencing reads not relevant to said fusion detection, hence leaving room for the detection of more fusions in parallel or higher multiplexing of patients per NGS run.

The invention may be particularly directed to the design of so-called low overlap probes, comprising universal and specific probes. The probes may be defined by the number of base pairs after the fusion breakpoint region that overlaps the secondary partner, wherein all the probes are of constant total length of 120 bp (i.e., 100% probe length). Universal probes (or 0 bp probes) do not overlap the secondary fusion partner and cover only the primary partner up to the edge of the breakpoint. Specific probes start in the primary fusion partner and overlap the secondary fusion partner and up to 10 bp, 20 bp, 30 bp, 40 bp or 50 bp beyond the fusion breakpoint (i.e., 9%, 17%, 25%, 33% or 42% of a total probe length) (FIG. 1B). These low overlap probes capture secondary partner reads resulting from the targeted fusion gene (FIG. 2A, 3A vs. FIG. 2B-D and FIG. 3B-D) and avoid capturing reads stemming from the WT counterpart.

The invention may be further directed to the mix of a universal probe and specific low overlap probes with overlap up to 10 bp, 20 bp, 30 bp, and 40 bp to a secondary fusion partner. This mix of overlap probes may capture more fusion fragments than 0 bp or 50 bp probes alone, as shown in Example 2 and 3. Only a mix of low overlap probes allows to reduce reads of WT secondary partner as compared to reads obtained using high overlap probes.

The invention may be further directed to the mix of a universal probe and specific low overlap probes with overlap up to 10 bp, 20 bp, 30 bp, 40 bp and 50 bp to a secondary fusion partner and the mix of a universal probe and specific low overlap probe with overlap up to 50 bp to a secondary fusion partner. These mixes of low overlap probes capture similar or higher number of fusion fragments as 0 bp probes alone, with some variation depending on the fusion in question as shown in Example 4. However, only a mix of low overlap probes may allow to reduce reads of WT secondary partner as compared to reads obtained using high overlap probes.

In an embodiment, a probe set comprises at least one probe comprising a first portion of the probe complementary to a primary nucleotide portion of a target nucleic acid, and a second portion of the probe complementary to a secondary nucleotide portion of the target nucleic acid, wherein the probe overlaps a breakpoint between the primary and the secondary nucleotide portion of the target nucleic acid, and wherein the length of second portion of the probe represents about 1% to about 42% of a total probe length, and at least one further probe complementary only to the primary nucleotide portion of the target nucleic acid, wherein the further probe does not overlap a breakpoint between the primary and the secondary nucleotide portion of the target nucleic acid.

In an embodiment, a probe set comprises at least two probes comprising a first portion of the probe complementary to a primary nucleotide portion of a target nucleic acid, and a second portion of the probe complementary to a secondary nucleotide portion of the target nucleic acid, wherein said probes overlap a breakpoint between the primary and the secondary nucleotide portion of the target nucleic acid, and wherein the length of second portion of the probe represents about 1% to about 42% of a total probe length, and wherein said probes have different length of the second portion of the probe.

In an embodiment, a probe comprises a first portion of the probe complementary to a primary nucleotide portion of a target nucleic acid, and a second portion of the probe complementary to a secondary nucleotide portion of a target nucleic acid, wherein the probe overlaps a breakpoint between the primary and the secondary nucleotide portion of the target nucleic acid, and wherein the length of second portion of the probe represents about 1% to about 42% of a total probe length.

In an embodiment, a probe, or a probe set according to the invention, includes the length of second portion of the probe to represent about 1%, 9%, 17%, 25%, 33% or 42% of a total probe length. The length of the second portion of the probe may represent a segment of the total length, the segment of the total length may be from the group consisting of: 1%, 9%, 17%, 25%, 33% or 42% of a total probe length. In an embodiment, a first portion of the probe is complementary to a primary nucleotide portion of a target nucleic acid that is selected from a fusion gene or transcript encoding primary fusion partner, or an exon skipping transcript encoding one exon, and a second portion of the probe is complementary to a secondary nucleotide portion of a target nucleic acid that is selected from a fusion gene or transcript encoding secondary fusion partner, or an exon skipping transcript encoding secondary exon.

According to an embodiment, the primary nucleotide portion of the target nucleic acid is the primary fusion partner that is a kinase molecule, and the secondary nucleotide portion of the target nucleic acid is the secondary fusion partner that is a non-kinase molecule. According to an embodiment, the probes of the invention are suitable for the capture and detection of fusion gene and thus DNA molecule. According to an embodiment, the probes of the invention are suitable for the capture and detection of fusion gene transcript and/or exon skipping transcript and thus RNA molecule.

The probes of the invention may be suitable for the capture and detection of known or novel fusion gene partners. Further, the probes of the invention may be suitable for the capture and detection of at least one fusion gene and/or exon skipping. The invention may provide a kit comprising at least one probe or a probe set according to the invention. Further, the invention may provide a composition comprising at least one probe or a probe set according to the invention.

According to an embodiment, the invention provides at least one probe or a probe set for use in targeted enrichment DNA-sequencing or RNA-sequencing. According to an embodiment, the invention provides a method for detection of a gene fusion and/or exon skipping in a sample comprising a step of hybridizing of at least one probe or a probe set according to the invention to the complementary portion of the target nucleic acid.

In an embodiment, the invention provides a method of targeted DNA-seq or RNA-seq with a target capture (i.e., hybridization capture-based targeted sequencing) comprising the steps of: providing a sample material comprising nucleic acids; preparing a nucleic acid sequencing library: hybridizing at least one probe or a probe set of the invention to target nucleic acids; amplifying nucleic acids; sequencing nucleic acids; and analyzing nucleic acids sequences obtained in step e).

According to an embodiment, the invention provides a method of diagnosing or monitoring of a cancer, comprising a step of hybridizing of at least one probe according to the invention or a probe set according to the invention to the complementary portions of the target nucleic acids present in a sample.

In an embodiment, the invention provides a method of diagnosing or monitoring of a cancer, wherein if the presence of an oncogenic fusion gene and/or exon skipping is detected in a patient sample, it indicates the presence of a cancer. According to an embodiment, the invention provides use of at least one probe or a probe set according to the invention in a method of detection of a fusion gene and/or exon skipping, preferably of the fusion gene present in a cancer.

DESCRIPTION OF THE FIGURES

FIG. 1A shows a high overlap probe design, where probes overlap up to 60 bp or 90 bp to a secondary fusion partner. Panel A) also shows a mix of high overlap probes (60 bp and 90 bp) with a low overlap probe (30 bp) as used in Example 2 and 3. FIG. 1B shows a low overlap probe design according to the invention where probes overlap 10 bp, 20 bp, 30 bp, 40 bp, or 50 bp to a secondary fusion partner.

FIG. 23) 0 bp probe: FIG. 2C) 50 bp probe and FIG. 2D) mix of 0 bp, 10 bp, 20 bp, 30 bp and 40 bp probes. Numbers on the left side of plots B-D represent the number of unique molecules that include the breakpoint region supporting the fusion (considering 3 million fragments input), percentages on the right side of the plot represent the percentage of unique molecules that support the fusion compared to the total unique molecules in the region.

FIG. 3B) 0 bp probe: FIG. 3C) 50 bp probe and FIG. 3D) mix of 0 bp, 10 bp, 20 bp, 30 bp and 40 bp probes. Numbers on the left side of plots B-D represent the number of unique molecules that include the breakpoint region supporting the fusion (considering 3 million fragments input), percentages on the right side of the plot represent the percentage of unique molecules that support the fusion compared to the total unique molecules in the region.

DETAILED DESCRIPTION

Figure 1A:
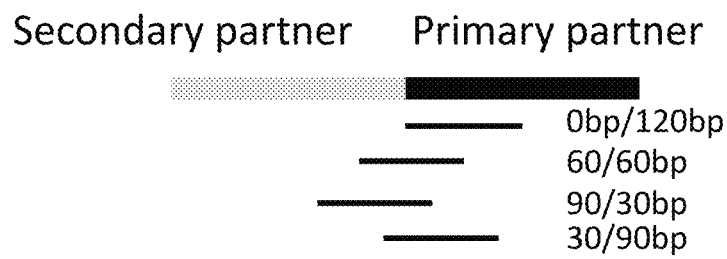
FIGS. 1A-1B shows a universal probe (a probe that does not overlap with a secondary fusion partner: called herein 0 bp) and examples of design of a specific probe (a probe which does overlap with a secondary fusion partner), and where all the probes are of constant total length of 120 bp.

The "nucleic acid molecule" may be chosen from known nucleic acid molecules, such as RNA (ribonucleic acid). DNA (deoxyribonucleic acid), LNA (locked nucleic acid), PNA (peptide nucleic acid), cDNA (complementary DNA) and others.

The term "fusion gene" or "gene fusion" or "fusion nucleic acid molecule" or "hybrid gene" or "chimeric gene" or "chimeric transcript" refers to a gene formed from two or more previously independent genes and includes all or a fragment of a first gene and all or a fragment of the second and/or subsequent gene. Fusion genes normally comprise two partners: (i) a primary fusion partner or gene, which is often a kinase gene, and (ii) a secondary fusion partner or gene. Fusion genes occur as a result of chromosomal rearrangements such as translocations, inversions and deletions and can lead to chimeric RNAs and proteins. Fusion genes have been found in all main types of human neoplasia (i.e., benign, potentially malignant, or malignant (cancer)). Fusion genes are important clinical biomarkers that guide diagnosis, inform prognosis and support treatment decisions.

The term "breakpoint" refers to the nucleotide position in the chromosome or transcript where two distal genomic regions are brought together either as a consequence of a genomic rearrangement or splicing. Further, the term "breakpoint" refers to a point between a primary and a secondary nucleotide portion of a target nucleic acid, such as between primary and secondary fusion partner of a fusion gene or transcript, and between one exon and second exon of exon skipping transcript (also called exon junction).

As such, a primary and a secondary nucleotide portion of a target nucleic acid, such as primary and secondary fusion partner of a fusion gene or transcript, and one exon and second exon of exon skipping transcript, are defined and separated by the breakpoint. It is understood that a secondary nucleotide portion of a target nucleic acid starts at a breakpoint. Often, a primary nucleotide portion of a target nucleic acid may be defined at 3' of the breakpoint and can be called a 3' partner. Often, a secondary nucleotide portion of a target nucleic acid may be at 5' of the breakpoint and can be called a 5' partner.

The term "fusion" or "fusion molecule" includes any fusion molecule such as gene, gene product (cDNA, mRNA, or polypeptide) and variant thereof that includes all or a fragment of a primary fusion gene or partner and all or a fragment of a secondary fusion gene or partner.

The term "known fusion" or "known gene fusion" or "known fusion gene" refers to the fusion gene wherein all or a fragment of a first gene (a primary fusion partner) and all or a fragment of a second gene (a secondary fusion partner) is known. There is an ongoing effort to catalogue gene fusions and describe their role in cancer e.g., COSMIC: catalogue of somatic mutations in cancer (Tate et al. 2019. *COSMIC: the Catalogue Of Somatic Mutations In Cancer Nucleic Acids Res.* 47(D1):D941-D947), Mitelman Database of Chromosome Aberrations and Gene Fusions in Cancer and Chimer D B (Jang et al., 2020. Chiner D B 4.0: an updated and expanded database of fusion genes. *Nucleic Acids Res.* 48(D1):D817-D824).

Conventional nomenclature to describe fusion genes is used herein, and for example includes:

e.g., fusion genes abbreviations (5'-3'), such as FGFR3-TACC3, wherein FGFR3 is abbreviation from Fibroblast Growth Factor Receptor 3 and is the primary fusion gene and TACC3 is abbreviation from Transforming acidic coiled-coil-containing protein 3 and is the secondary fusion gene, or PAX8-PPARG, wherein PAX8 is abbreviation from paired box gene 8 and is the secondary fusion gene and PPARG is abbreviation from Peroxisome Proliferator Activated Receptor Gamma and is the primary fusion gene, or
  e.g., fusion gene abbreviations (5'-3') containing relevant transcript and exons. For example an FGFR3:BAIAP2L1 (NM_000142:e17:NM_018842:e2) fusion comprises a 5' FGFR3 transcript NM_00142 up to exon 17 fused with a 3' partner BAIAP2L 1 transcript NM_018842 starting at exon 2.

The term "unknown fusion" or "novel fusion" or "partner agnostic fusion" or "unknown fusion gene" or "novel fusion gene" or "partner agnostic gene fusion" refers to the fusion gene wherein novel fusion genes or secondary gene partners or isoform has not yet been identified.

The term "kinase" or "kinase molecule" refers to a group of enzymes that catalyze the transfer of phosphate groups from a high-energy phosphate-containing molecule (such as ATP) to a substrate. Kinase enzymes include protein kinases (such as cyclin dependent kinases (CDKs), mitogen-activated protein kinases (MAPKs)), lipid kinases (such as phosphatidylinositol kinases, sphingosine kinase (SK)), carbohydrate kinases (such as hexokinase, phosphofructokinase (PFK)), kinases that act on nucleotides (DNA and RNA), kinases that act on other small molecules that are substrates of these kinases (for example creatine, phosphoglycerate, riboflavin, dihydroxyacetone, shikimate, and others). The term "kinase gene" or "kinase transcript" refers to a group of genes or transcripts that do encode a kinase molecule.

The term "non-kinase" or "non-kinase gene" or "non-kinase transcript" refers to a group of genes or transcripts that do not encode a kinase protein.

The term "exon skipping" refers to a form of RNA splicing that cause cells to exclude one or more contiguous exons from the messenger RNA. The "exon" refers to a region remaining in the nucleotide sequence of a mature transcript, among the nucleotide sequence of a gene. It is understood that the exon skipping can be caused by deletions, mutations or occur as a consequence of splicing regulation. The included exons, immediately flanking the skipped exon, present in the nucleic acid molecule can be detected using probes and principles disclosed herein.

The term "RNA sequencing" or "RNAseq" or "RNA-seq" or "transcriptome profiling" or "RNA high-throughput sequencing" or "massive parallel RNA sequencing" or "next-generation sequencing of cDNA" refers to a sequencing technique which uses next-generation sequencing (NGS) to reveal the presence and quantity of RNA in a biological sample at a given moment, by analyzing the cellular transcriptome.

The term "targeted RNA-sequencing" or "targeted RNA-seq" refers to RNA-seq coupled with specific targets enrichment, which can be done, for instance by target capture or amplicon-based approaches (amplicon sequencing). This method allows for selecting and sequencing specific transcripts of interest (i.e., to enrich for RNA transcripts of interest or enrichment). Similarly, the term "targeted DNA-sequencing" or "targeted DNA-seq" refers to DNA-seq coupled with specific targets enrichment, which can be done, for instance by target capture or amplicon-based approaches (amplicon sequencing).

The term "targeted RNA-seq/DNA-seq by target capture" or "(RNA/DNA) CaptureSeq" or "hybridization capture (sequencing)" or "target capture method" or "hybridization capture-based target enrichment for NGS" refers to an enrichment technique comprising a step of hybridization capture. In this technique RNA or DNA sequencing libraries are subjected to hybridization capture using probes specifically designed to isolate the sequences of interest and linked to a biochemical moiety (typically biotin). These target enriched libraries are then amplified and sequenced.

The term "probe" or "bait" or "(probe) nucleic acid molecule" or "capture probe" or "(DNA/RNA) oligonucleotide (capture) probe" refers to a nucleic acid molecule that can hybridize to a target nucleic acid molecule. In the context of fusion gene and exon skipping detection, a probe is capable of hybridizing or annealing to the nucleic acid molecule of a fusion gene/transcript and/or transcript resulting from exon skipping. If a probe is hybridizing/annealing only to the nucleic acid molecule of a primary fusion gene (partner), it allows the detection of any fusion involving that gene and such a probe is herein referred to as a universal probe. If a probe is hybridizing/annealing to the nucleic acid molecule of a primary fusion gene (partner) and over the breakpoint hence into the secondary fusion gene (partner), it allows the detection of known fusion genes and such a probe is herein referred to as a specific probe.

The term "target nucleic acid" refers to a nucleic acid region within a gene or a transcript that may be captured by the probe of the present invention; for example, a gene that may form a fusion gene and a transcript in which exon skipping may occur.

Probes

In an embodiment, a probe may comprise a first portion of the probe complementary to a primary nucleotide portion of a target nucleic acid, and a second portion of the probe complementary to a secondary nucleotide portion of the target nucleic acid, wherein said probe overlaps a breakpoint between said primary and secondary nucleotide portion of a target nucleic acid, and wherein the length of second portion of the probe represents about 1% to about 42% of a total probe length.

It is understood that wherein in a probe the length of second portion of the probe may represent about 1% to about 42% of a total probe length, it means that a second portion of the probe overlaps with a second part of a target nucleic acid by this percentage of its total length.

It is understood that the probe may comprise a portion of the probe complementary to a primary nucleotide portion of a target nucleic acid, and another portion of the probe complementary to a secondary nucleotide portion of the target nucleic acid.

It is understood that the probe complementary to a primary and a secondary nucleotide portion of a target nucleic acid is a specific probe and allows for detection of, for example, known fusion gene or an exon skipping.

In one embodiment, a target nucleic acid is a fusion gene or transcript, wherein a primary nucleotide portion of said target nucleic acid is a fusion gene or transcript encoding primary fusion partner, and a secondary nucleotide portion of said target nucleic acid is a fusion gene or transcript encoding a secondary fusion partner.

In one embodiment, a target nucleic acid is an exon skipping transcript, wherein a primary nucleotide portion of said target nucleic acid is an exon skipping transcript encoding one exon, and a secondary nucleotide portion of said target nucleic acid is an exon skipping transcript encoding secondary exon.

In one embodiment, a target nucleic acid is selected from DNA, RNA and cDNA.

In one embodiment, a probe may comprise a first portion of the probe complementary to a primary nucleotide portion of a target nucleic acid that is a fusion gene or transcript encoding primary fusion partner, or an exon skipping transcript encoding one exon, and a second portion of the probe complementary to a secondary nucleotide portion of the target nucleic acid that is a fusion gene or transcript encoding a secondary fusion partner, or an exon skipping transcript encoding secondary exon, and wherein said probe overlaps a breakpoint between said primary and secondary nucleotide portion of a target nucleic acid, and wherein the length of second portion of the probe represents about 1% to about 42% of a total probe length.

The nucleotide length of a second portion of the probe complementary to a secondary nucleotide portion of a target nucleic acid expressed as a percentage of a total probe length may be, but not limited to, for example, 1% or more, 9% or more, 17% or more, 25% or more, 33% or more, about 42%, and no longer than about 42%; and about 1%, 9% or less, 17% or less, 25% or less, 33% or less, 42% or less; for example, 1% to 42%, 1% to 33%, 1% to 25%, 1% to 17%, 1% to 9%. Preferably, the length of the second portion of the probe expressed as a percentage of a total probe length is selected from about 1%, 9%, 17%, 25%, 33% and 42%.

In one embodiment, a probe may comprise a first portion of the probe complementary to a primary nucleotide portion of a target nucleic acid, and a second portion of the probe complementary to a secondary nucleotide portion of the target nucleic acid, wherein said probe overlaps a breakpoint between said primary and secondary nucleotide portion of a target nucleic acid, and wherein said second portion of the probe is 1 to about 50 base pair (bp) long and a total probe length is of about 120 bp.

In one embodiment, a probe may comprise a first portion of the probe complementary to a primary nucleotide portion of a target nucleic acid that is a fusion gene or transcript encoding primary fusion partner, or an exon skipping transcript encoding one exon, and a second portion of the probe complementary to a secondary nucleotide portion of a target nucleic acid that is a fusion gene or transcript encoding a secondary fusion partner, or an exon skipping transcript encoding secondary exon, and wherein said probe overlaps a breakpoint between said primary and secondary nucleotide portion of a target nucleic acid, and wherein said second portion of the probe is 1 to about 50 base pair (bp) long and a total probe length is of about 120 bp.

The nucleotide length of a second portion of the probe complementary to a secondary nucleotide portion of a target nucleic acid may be, but not limited to, for example, 1 or more, 10 or more, 20 or more, 30 or more, 40 or more, about 50 and no longer than about 50; and 10 or less, 20 or less, 30 or less, 40 or less, 50 or less; for example, 10 to 50, 10 to 40, 10 to 30, 10 to 20. Preferably, the nucleotide length of a second portion of the probe complementary to a secondary nucleotide portion of a target nucleic acid is selected from about 10, 20, 30, 40 and 50.

The total nucleotide length of a probe may be, but not limited to, for example, 20 or more, 40 or more, 60 or more, 80 or more, 100 or more, 110 or more or 115 or more; and 220 or less, 200 or less, 180 or less, 160 or less, 140 or less, 130 or less or 125 or less: for example, 20 to 220, 60 to 180, 100 to 140, 110 to 130, 115 to 125 or 120. Preferably, the nucleotide length of a probe is about 120.

In one embodiment, is provided a probe complementary only to a primary nucleotide portion of a target nucleic acid, wherein said probe does not overlap a breakpoint between a primary and a secondary nucleotide portion of a target nucleic acid. In this embodiment a second portion of the probe is not present. In this embodiment a second portion of the probe is 0 bp (0 bp probe). It is understood that said probe is a universal probe and allows for detection of unknown fusion gene.

The nucleotide length of a universal probe may be, but not limited to, for example, 20 or more, 40 or more, 60 or more, 80 or more, 100 or more, 110 or more or 115 or more; and 220 or less, 200 or less, 180 or less, 160 or less, 140 or less, 130 or less or 125 or less; for example, 20 to 220, 60 to 180, 100 to 140, 110 to 130, 115 to 125 or 120. Preferably, the nucleotide length of a probe is 120.

According to an embodiment, a probe only complementary to a primary nucleotide portion of a target nucleic acid (a universal probe, or 0 bp probe), and a probe of the invention comprising a second portion of the probe of 1 to about 50 bp long are referred herein as low overlap probes. A probe comprising a second portion of the probe of more than 50 bp long is referred herein as a high overlap probe. The low overlap probe design according to the invention and high overlap probe design is described in Example 1 and shown on FIGS. 1A-1B.

In one embodiment, a probe may comprise a first portion of the probe complementary to a fusion gene or transcript encoding primary fusion partner, wherein the primary fusion partner is preferably a kinase molecule, and a second portion of the probe complementary to a fusion gene or transcript encoding a secondary fusion partner, wherein the secondary fusion partner is preferably a non-kinase molecule, and wherein said probe overlaps a breakpoint between said primary and secondary fusion partners according to the invention described herein.

In one embodiment provided is a probe of the invention comprising a first portion of the probe complementary to a fusion gene or transcript encoding primary fusion partner, wherein said primary fusion partner is a kinase molecule. It is understood that such a kinase molecule includes any known kinase. Examples of kinases include but are not limited to protein k-mases (such as CDKs, MAPKs), lipid kinases (such as phosphatidylinositol kinases, SK), carbohydrate kinases (such as hexokinase, PFK), kinases that act on nucleotides (DNA and RNA), and kinases that act on other small molecules. Preferably, kinases are tyrosine kinases and serine/threonine kinases. Examples of specific kinases include but are not limited to ALK, RET, ROS, MET, BRAF, NTRKs and the like.

In one embodiment provided is a probe of the invention comprising a second portion of the probe complementary to a fusion gene or transcript encoding a secondary fusion partner, wherein said secondary fusion partner is a non-kinase molecule. It is understood that such a non-kinase molecule may include any known non-kinase molecules. Examples of non-kinases include but are not limited to EML4, CD74, ETV6, TACC3, LMNA, SLC34A2 and the like.

Table 1 provides examples of fusion genes that can be captured and detected by the probes of the invention.

TABLE 1

| Fusion name | Main partner (Kinase or not-kinase) | Main partner |
|---|---|---|
| CD74-ROS1 | Kinase | ROS1 |
| EML4-ALK | Kinase | ALK |
| ETV6-NTRK3 | Kinase | NTRK3 |
| FGFR3-BAIAP2L1 | Kinase | FGFR3 |
| FGFR3-TACC3 | Kinase | FGFR3 |
| KIF5B-RET | Kinase | RET |
| LMNA-NTRK1 | Kinase | NTRK1 |
| NCOA4-RET | Kinase | RET |
| PAX8-PPARG | non-kinase (nuclear receptor) | PPARG |
| SLC34A2-ROS1 | Kinase | ROS1 |
| SLC45A3-BRAF | Kinase | BRAF |
| TPM3-NTRK1 | Kinase | NTRK1 |

In one embodiment, the probes of the invention are made of DNA or RNA, preferably are made of DNA.

In the context of probe description, the terms "complementary" and "homologous" are used interchangeably.

In one embodiment, is provided a probe according to the invention comprising any of the following nucleotide sequences: (a) a nucleotide sequence comprising at least consecutive 20, 40, 60, 80, 100, 110, 115 or 120 nucleotides complementary to a primary and/or secondary nucleotide portion of a target nucleic acid; (b) a nucleotide sequence having the nucleotide sequence (a) in which one or more nucleotides are added, deleted, and/or substituted; (c) a nucleotide sequence having an identity of, for example, 70% or more, 80% or more, 90% or more, 95% or more, 97% or more, 98% or more or 99% or more with the nucleotide sequence (a); and (d) the nucleotide sequence of a nucleic acid hybridizing with a primary and/or secondary nucleotide portion of a target nucleic acid having at least consecutive 20, 40, 60, 80, 100, 110, 115 or 120 nucleotides under stringent conditions.

In one embodiment, the probes of the invention enrich (i.e., capture) for the gene fusion (DNA) or transcript (RNA) of interest.

In one embodiment, the probes of the invention are suitable for the capture and detection of exon skipping and/or fusion genes.

In one embodiment, the probes of the invention are suitable for the capture and detection of a fusion gene comprising more than two partners.

In another embodiment, the probes of the invention are linked to detectable labels such as biotin, magnetic beads, fluorophores, radioisotopes, nanoparticles. It is understood that such probes can be used for targeted enrichment methods.

In another embodiment, the probes of the invention are linked to a microarray such as DNA microarrays, cDNA microarrays, SNP microarrays. It is understood that such probes can be used for the hybrid capture reaction.

In another embodiment, the probe of the invention has a sequence selected from SEQ ID NO: 1 to SEQ ID NO: 75.

In one embodiment, provided is a universal probe selected from SEQ ID NO: 4, SEQ ID NO: 13, SEQ ID NO: 19, and SEQ ID NO: 20 to SEQ ID NO: 26.

In one embodiment, provided is a probe of the invention wherein a second portion of the probe is 10 bp long and a total probe length is 120 bp, selected from SEQ ID NO: 6, SEQ ID NO: 15, and SEQ ID NO: 37 to SEQ ID NO: 46.

In one embodiment, provided is a probe of the wherein a second portion of the probe is 20 bp long and a total probe length is 120 bp, selected from SEQ ID NO: 7, SEQ ID NO: 16, and SEQ ID NO: 47 to SEQ ID NO: 56.

In one embodiment, provided is a probe of the invention wherein a second portion of the probe is 30 bp long and a total probe length is 120 bp, selected from SEQ ID NO: 1, SEQ ID NO: 8, SEQ ID NO: 12, SEQ ID NO: 17 and SEQ ID NO: 57 to SEQ ID NO: 66.

In one embodiment, provided is a probe of the invention wherein a second portion of the probe is 40 bp long and a total probe length is 120 bp, selected from SEQ ID NO: 9, SEQ ID NO: 18, and SEQ ID NO: 67 to SEQ ID NO: 76.

In one embodiment, provided is a probe of the invention wherein a second portion of the probe is 50 bp long and a total probe length is 120 bp, selected from SEQ ID NO: 5, SEQ ID NO: 14, and SEQ ID NO: 27 to SEQ ID NO: 36.

In one embodiment, provided is a method of a preparation of the probes according to the invention.

Standard methods of chemical synthesis of DNA or RNA probes can be used, such as described in McBride L J and Caruthers M H, 1983, *Tetrahedron Letters* 24(3): 245-248.

In one embodiment, provided is a method of a preparation of the probes according to the invention comprising oligonucleotide synthesis upon microarrays with lengths ranging from about 60 to about 120 bases or about 80 to about 120 bases.

The oligonucleotide pool (probes pool) is modified by known process before enrichment step, so that to include a detectable label such as biotin, magnetic beads, fluorophores, radioisotopes, or nanoparticles, such as with methods described in Klöcker et al., 2020. *Chem. Soc. Rev.* 49, p. 8749-8773.

It is understood that detached probes can be used for solution phase methods, whereas probes on microarrays can be used for surface phase methods.

Set of Probes

In another embodiment, provided is a set (a combination or a mix or a pool) of the probes according to the invention.

In one embodiment, provided is a probe set comprising at least two, at least three, at least four, at least five or at least six probes according to the invention.

In one embodiment, provided is a probe set comprising at least 10, at least 20, at least 40, at least 50, at least 100, at least 200, at least 300, at least 400 or at least 500 probes according to the invention.

In one embodiment, a probe set according to the invention comprises at least one universal probe and at least one specific probe according to the invention.

In one embodiment, a probe set may comprise at least one probe comprising a first portion of the probe complementary to a primary nucleotide portion of a target nucleic acid, and a second portion of the probe complementary to a secondary nucleotide portion of the target nucleic acid, wherein said probe overlaps a breakpoint between said primary and secondary nucleotide portion of a target nucleic acid, and wherein the length of second portion of the probe represents about 1% to about 42% of a total probe length and at least one further probe complementary only to a primary nucleotide portion of a target nucleic acid, wherein said probe does not overlap a breakpoint between a primary and a secondary nucleotide portion of a target nucleic acid.

In one embodiment, a probe set may comprise at least one probe comprising a first portion of the probe complementary to a primary nucleotide portion of a target nucleic acid, and a second portion of the probe complementary to a secondary nucleotide portion of the target nucleic acid, wherein said probe overlaps a breakpoint between said primary and secondary nucleotide portion of a target nucleic acid, and wherein said second portion of the probe is 1 to about 50 base pair (bp) long and a total probe length is of about 120 bp and at least one further probe complementary only to a primary nucleotide portion of a target nucleic acid, wherein said probe does not overlap a breakpoint between a primary and a secondary nucleotide portion of a target nucleic acid.

It is understood that a probe set comprising at least one universal probe and at least one specific probe of the invention is suitable for the capture and detection of known and novel fusion gene partners.

In one embodiment, a probe set according to the invention comprises at least two specific probes according to the invention.

In one embodiment, a probe set may comprise at least two probes comprising a first portion of the probe complementary to a primary nucleotide portion of a target nucleic acid, and a second portion of the probe complementary to a secondary nucleotide portion of the target nucleic acid, wherein said probe overlaps a breakpoint between said primary and secondary nucleotide portion of a target nucleic acid, and wherein the length of second portion of the probe represents about 1% to about 42% of a total probe length.

In one embodiment, a probe set may comprise at least two probes comprising a first portion of the probe complementary to a primary nucleotide portion of a target nucleic acid, and a second portion of the probe complementary to a secondary nucleotide portion of the target nucleic acid, wherein said probe overlaps a breakpoint between said primary and secondary nucleotide portion of a target nucleic acid, and wherein said second portion of the probe is 1 to about 50 base pair (bp) long and a total probe length is of about 120 bp.

It is understood that a probe set comprising at least two specific probes of the invention is suitable for the capture and detection of known fusion gene partners.

In another preferable embodiment, a probe set according to the invention comprises at least two specific probes according to the invention that have different length of the second portion of the probe.

In one embodiment, a probe set according to the invention comprises probes that hybridize to different target nucleic acids, so that multiple different target nucleic acids can be captured and detected with one probe set.

In one embodiment, a probe set according to the invention comprises probes that hybridize to the same primary nucleotide portion of a target nucleic acid such as a fusion gene or transcript encoding primary fusion partner, or an exon skipping transcript encoding one exon. An exemplary probe set comprises both the specific and/or universal probes that hybridize to the same primary fusion gene that is PPARG or FGFR3.

In one embodiment, a probe set according to the invention comprises the probes that hybridize to at least 2, at least 3, at least 4, at least 5, at least 10, at least 20, at least 50 or at least 100 different primary nucleotide portion of a target nucleic acids such as fusion genes or transcripts encoding primary fusion partners, or an exon skipping transcripts encoding one exon.

In one embodiment, a probe set according to the invention comprises at least one universal probe complementary only to a primary nucleotide portion of a target nucleic acid and at least one, at least two, at least three, at least four, or at least five probes wherein the length of second portion of the probe represents about 1% to about 42% of a total probe length (specific probes) such as about 1%, 9%, 17%, 25%, 33% and/or 42%.

In one embodiment, a probe set according to the invention comprises at least one universal probe complementary only to a primary nucleotide portion of a target nucleic acid and at least one, at least two, at least three, at least four, or at least five probes wherein a second portion of the probe is about 1 to about 50 bp long (specific probes) such as about 10 bp, 20 bp, 30 bp, 40 bp and/or 50 bp long and a total probe length is of about 120 bp.

In one embodiment, a probe set according to the invention comprises at least one universal probe complementary only to a primary nucleotide portion of a target nucleic acid and at least one probe wherein the length of second portion of the probe represents 42% of a total probe length (specific probe).

In one embodiment, a probe set according to the invention comprises at least one universal probe complementary only to a primary nucleotide portion of a target nucleic acid and at least one probe wherein a second portion of the probe is 50 bp long and a total probe length is of about 120 bp.

In one embodiment, a probe set according to the invention comprises at least one universal probe complementary only to a primary nucleotide portion of a target nucleic acid and at least five probes wherein the length of second portion of the probe represents about 1%, 9%, 17%, 25%, 33% and/or 42% of a total probe length (specific probes).

In one embodiment, a probe set according to the invention comprises at least one universal probe complementary only to a primary nucleotide portion of a target nucleic acid and at least five probes wherein a second portion of the probe is about 10 bp, 20 bp, 30 bp, 40 bp and/or 50 bp long and a total probe length is of about 120 bp (specific probes).

In one embodiment, a probe set according to the invention comprises at least two probes wherein the length of second portion of the probe represents about 1% to about 42% of a total probe length, such as about 1%, 9%, 17%, 25%, 33% and/or 42% (specific probes).

In one embodiment, a probe set according to the invention comprises at least two, at least three, at least four or at least five probes wherein the length of second portion of the probe represents about 1% to about 42% of a total probe length, such as about 1%, 9%, 17%, 25%, 33% and/or 42% (specific probes). Preferably, a probe set according to the invention comprises at least five probes wherein the length of second portion of the probe represents about 1%, 9%, 17%, 25%, 33% and/or 42% of a total probe length.

In one embodiment, a probe set according to the invention comprises at least two probes wherein a second portion of the probe is about 1 to about 50 bp long, such as about 10 bp, 20 bp, 30 bp, 40 bp and/or 50 bp long and a total probe length is of about 120 bp (specific probes).

In one embodiment, a probe set according to the invention comprises at least two, at least three, at least four or at least five probes wherein a second portion of the probe is about 1 to about 50 bp long (specific probes), such as about 10 bp, 20 bp, 30 bp, 40 bp and/or 50 bp long and a total probe length is of about 120 bp (specific probes). Preferably, a probe set according to the invention comprises at least five probes wherein a second portion of the probe is about 10 bp, 20 bp, 30 bp, 40 bp and/or 50 bp long and a total probe length is of about 120 bp.

It is understood that a probe set according to the invention may be a composition or a reaction a mixture, optionally further comprising a target nucleic acid molecule, such as a fusion nucleic acid molecule (a fusion gene/transcript) and/or exon skipping nucleic acid molecule (exon skipping transcript).

It is understood that a probe set according to the invention may be a reaction a mixture further comprising a target nucleic acid molecule derived from a patient sample.

The terms "a set of probes", "a probe set", or "a probe pool" are used interchangeably.

In one embodiment, is provided a probe set according to the invention further comprising any known probe in the art.

Methods and Uses of the Probes

The probes of the invention may be designed to advantageously reduce capturing the WT secondary fusion partner counterpart.

According to a particular aspect, the invention provides at least one probe or a probe set for detecting at least one fusion gene and/or exon skipping.

According to another particular aspect, the invention provides use of at least one probe or a probe set for detecting at least one fusion gene and/or exon skipping.

According to a particular aspect, the invention provides at least one probe or a probe set for detecting at least one fusion gene, wherein said fusion gene is known or unknown (i.e., novel or partner agnostic fusion).

According to a particular aspect, the invention provides at least one probe or a probe set for use in targeted enrichment DNA- or RNA-sequencing.

According to another particular aspect, the invention provides use of at least one probe or a probe set in targeted enrichment DNA- or RNA-sequencing methods.

According to a particular aspect, the invention provides at least one probe or a probe set for use in Next-Generation Sequencing (NGS)-based targeted enrichment DNA- or RNA-sequencing.

According to another particular aspect, the invention provides use of at least one probe or a probe set in Next-Generation Sequencing (NGS)-based targeted enrichment DNA- or RNA-sequencing methods.

According to a particular aspect, the invention provides at least one probe or a probe set for use in methods such as microarrays, blotting, immobilization of probes in columns or beads for purification of target DNA and the like.

According to another particular aspect, the invention provides use of at least one probe or a probe set in methods such as microarrays, blotting, immobilization of probes in columns or beads for purification of target DNA and the like.

According to one embodiment, provided is a method for detection of a gene fusion and/or exon skipping in a sample comprising a step of hybridizing of at least one probe according to the invention or a probe set according to the invention to the complementary portions of the target nucleic acids.

According to one embodiment, provided is a method of targeted or RNA-seq with a target capture (i.e., hybridization capture sequencing) comprising the steps of: a) providing a sample material comprising nucleic acids; b) preparing a nucleic acid sequencing library; c) hybridizing at least one probe or a probe set of the invention to target nucleic acids; d) amplifying nucleic acids; e) sequencing nucleic acids; and f) analyzing nucleic acids sequences obtained in step e.

According to one embodiment, provided is a method of targeted RNA-seq with a target capture wherein the step a) providing a sample material comprising nucleic acids comprises the steps of: a.1) providing a sample material comprising nucleic acids; a.2) optionally, selecting mRNA transcripts; a.3) optionally, depleting rRNA (ribosomal RNA); a.4) fragmenting mRNA transcripts.

Step a) and a.1)-a.4) may be performed according to any known method such as poly A selection (a.2 and a.3), hybridization-based rRNA depletion (a.3), chemical or enzymatic RNA fragmentation (a.4).

According to one embodiment, provided is a method of targeted RNA-seq with a target capture wherein the step b) preparing a nucleic acid sequencing library comprises the steps of: b.1) converting a sample RNA to cDNA (complementary DNA); b.2) optionally, converting double stranded cDNA into blunt-end DNA, followed by the addition of a non-template 3' dAMP (dA) nucleotide tail; b.3) optionally, ligating cDNA to sequencing adapters; b.4) optionally, amplifying cDNA-adapter product to generate whole transcriptomes libraries. Step b) and b.1)-b.4) may be performed according to any known method such as reverse transcription, double strand cDNA synthesis (b1), end repair and A-tailing (b2), enzymatic ligation (b3), PCR (b4). Step b.3 is necessary for preparation of a nucleic acid sequencing library for NGS.

According to one embodiment, provided is a method of targeted RNA-seq with a target capture wherein the step c) hybridizing at least one probe or a probe set of the invention to target nucleic acids (i.e., enriching for the sequences of interest) comprises the steps of: c.1) providing individual or pooled cDNA libraries obtained in step b); c.2) hybridizing at least one probe or a probe set of the invention to target libraries; c.3) washing away non-targeted cDNA/libraries; c.4) eluting targeted cDNA/libraries;

Step c) and c.1)-c.4) may be performed according to any known method such as target hybridization capture.

In one embodiment, step c.2) is performed by incubation of individual or pooled cDNA libraries with the probes, preferably at 65° C.

In one embodiment, step c.2) is performed by incubation of individual or pooled cDNA libraries with the probes linked a biochemical moiety, such as a biotin, wherein said probes anneal to the sequences of interest in the libraries and the annealed product is then captured using a system that specifically selects the biochemical moiety used, such as magnetic beads linked to streptavidin.

In one embodiment, the probes linked to a biotin and magnetic beads linked to streptavidin are used to capture said probes.

In step c.3) the probes annealed to the libraries are washed to remove non-specifically bound sequences and the resulting product is amplified by PCR (step d) and sequenced (step e).

It is understood that in step c) the probes hybridize to target nucleic acids under suitable conditions for hybridization and washing under which nucleotide sequences at least 60%, at least 65%, at least 70%, at least 75%, at least 80%, at least 85%, at least 90%, at least 95% or 100% identical to each other typically remain hybridized to each other.

Step d) amplifying nucleic acids may be performed according to any known method such as polymerase chain reaction (PCR).

Step e) sequencing nucleic acids may be performed according to any known method such as sequencing by synthesis (Illumina), ion semiconductor sequencing (Ion Torrent), single molecule real time (SMRT) sequencing (Pacific Biosciences), nanopore DNA/RNA sequencing (Oxford Nanopore Technologies), and the like.

Step f) analysis may be performed according to any known method such that the number of fragments supporting the presence of the gene fusion event(s) of interest are quantified.

It is understood that known gene fusions and novel gene fusions are, in particular, oncogenic gene fusions.

According to one embodiment, provided is a method of targeted DNA-seq or RNA-seq with a target capture, wherein a sample is obtained from a subject that has or is suspected of having a disease, preferably the disease is a cancer.

According to one embodiment, provided is a method of targeted DNA-seq or RNA-seq with a target capture, wherein if the presence of a fusion gene and/or exon skipping is detected in a sample, it indicates the presence of a cancer.

Compositions

According to another aspect of the invention provided is a composition comprising at least one probe according to the invention.

According to another aspect of the invention provided is a composition comprising at least one set of probes according to the invention.

According to a particular aspect, the compositions of the inventions are useful in the methods of the invention, in particular in methods of targeted DNA-seq or RNA-seq and methods of diagnosing or monitoring of a cancer.

According to a particular aspect, the composition of the inventions is a reaction a mixture, optionally further comprising the target nucleic acid molecule.

Kits

According to another aspect of the invention provided is a kit comprising at least one probe according to the invention and optionally instructional material.

According to another aspect of the invention provided is a kit comprising at least one set of probes according to the invention and optionally instructional material.

According to a particular aspect, the kits of the inventions are useful in the methods of the invention, in particular in methods of targeted DNA-seq or RNA-seq and methods of diagnosing or monitoring of a cancer.

Methods of Cancer Diagnosing and Monitoring

In one embodiment, expression of the fusion genes or exon skipping is detected in patient samples and suggesting presence of a cancer.

According to a particular aspect, the invention provides at least one probe or a set of probes for use in a method of detection of a fusion gene and/or exon skipping, preferably of a fusion gene and/or the exon skipping present in cancer.

According to another particular aspect, the invention provides use of at least one probe or a set of probes in a method of detection of a fusion gene and/or exon skipping, preferably of a fusion gene and/or the exon skipping present in cancer.

According to one embodiment, provided is a method of diagnosing or monitoring of a cancer, comprising a step of hybridizing of at least one probe according to the invention or a probe set according to the invention to the complementary portions of the target nucleic acids present in a sample.

According to a particular embodiment, provided is a method of diagnosing or monitoring of a cancer, comprising any methods of the invention as described herein.

According to another particular embodiment, provided is a method of diagnosing or monitoring of a cancer, comprising the steps of: a) providing a sample material comprising nucleic acids; b) preparing a nucleic acid sequencing library; c) hybridizing at least one probe or a probe set of the invention to target nucleic acids; d) amplifying nucleic acids: e) sequencing nucleic acids; and f) analyzing nucleic acids sequences obtained in step e).

According to one embodiment, provided is a method of diagnosing or monitoring of a cancer, wherein if the presence of a fusion gene and/or exon skipping is detected in a patient sample, it indicates the presence of a cancer.

According to one embodiment, provided is a method of diagnosing or monitoring of a cancer, wherein a sample is obtained from a subject that has or is suspected of having a disease, preferably the disease is a cancer.

According to one embodiment, provided is a method of diagnosing or monitoring of a cancer, wherein the detection of a presence of a fusion gene and/or exon skipping in a patient sample indicates the treatment for said patient.

According to one aspect, a sample is a patient sample and is in a form of tissue, blood, saliva, or cytological specimens/preparation (FFPE, smears), and the like.

Patients

In an embodiment, patients according to the invention are suffering from a cancer.

In another particular embodiment, patients according to the invention are suffering from lung cancer, cholangiocarcinoma, prostate cancer, pancreatic ductal adenocarcinoma, thyroid carcinoma, colorectal cancer, gastric cancer, glioblastoma, head and neck cancer, kidney cancer, endometrial cancers and the like.

In another particular embodiment, patients according to the invention are susceptible to suffer from a cancer.

In another particular embodiment, patients according to the invention are undergoing treatment for cancer.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

NON-LIMITING EXAMPLES

The following non-limiting examples further illustrate the invention but, of course, should not be construed as in any way limiting its scope.

Example 1: Probe Design

In a fusion gene there is a primary partner (often a kinase enzyme) which has relatively low levels of expression in its WT form (wild type), and a secondary partner, which is often a gene that has higher WT levels of expression. That means that when probe design is done, if the probes are designed such that they can capture the WT counterpart of the secondary partner there will be many reads consumed by WT form of the gene when compared to the fused form.

Figure 1B:
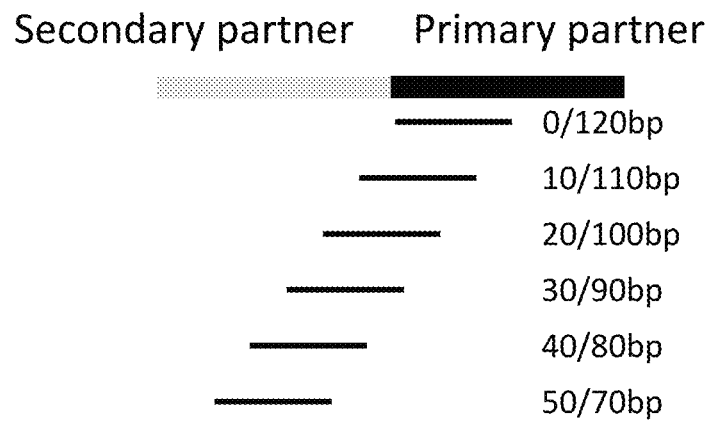

The following probes may be designed for: i) universal probes, that are probes which do not overlap with a secondary fusion partner, i.e., called herein 0 bp probes, wherein these probes may be of constant total length of 120 bp. (FIGS. 1A-1B). Theses probes may allow to capture novel fusions of the primary fusion partner; ii) specific probes, that are probes which do overlap with a secondary fusion partner, i.e., a second portion of the probe is at least 1 bp. In a high overlap probe design, specific probes overlap to about more than 50 bp such as up to 60 bp or 90 bp to secondary fusion partner, and where all the probes are of constant total length of 120 bp. (FIG. 1A). In a low overlap probe design (according to the invention), specific probes overlap up to 10 bp, 20 bp, 30 bp, 40 bp or 50 bp to secondary fusion partner, and where all the probes are of constant total length of 120 bp. (FIG. 1B).

Example 2: Comparison of Performance Between High Overlap Probe Design and Low Overlap Probe Design in Detection of FGFR3-TACC3 Fusion High overlap and low overlap probes performance was compared in detection of FGFR3-TACC3 fusion. FGFR3 is the primary fusion gene.

Material and Methods

RNA-seq libraries were prepared using 100 ng of RNA extracted from Seraseq® FFPE Tumor Fusion RNA v2 reference material. Individually barcoded w % bole-transcriptome libraries were then captured using the xGEN Lockdown IDTX probe-based capture technology using custom panels. The probes were designed according to the invention with a mix of probes containing high overlap probes mix (60 bp, 90 bp) with low overlap probes (30 bp) (FIG. 2A), or low overlap probes: 0 bp probes (FIG. 2B), or low overlap 50 bp probes (FIG. 2C), or a mix of 0 bp, 10 bp, 20 bp, 30 bp, and 40 bp low overlap probes (FIG. 2D), and including probes that target the FGFR3-TACC3 fusion. In this fusion gene FGFR3 is the primary fusion gene and TACC3 is the secondary fusion gene. Captured libraries were then sequenced using an Illumina MiSeq instrument. Data were analyzed by mapping the reads with BWA-MEM aligner to a home-made fusion synthetic genome and heat-map of fragments starts relative to fusion breakpoint were generated. The mix of probes contained probes targeting different gene fusions, for clarity only probes that target the FGFR3-TACC3 fusion are described and results of detection of the FGFR3-TACC3 fusion are reported.

The following probes may be used:

a) a mix of high overlap probes (60 bp and 90 bp) and low overlap probes (30 bp) (FIG. 2A):

| Probe name | Probe sequence | type |
| --- | --- | --- |
| Fusion::FGFR3::4:<br>1808632-1808661::4:<br>1741429-1741505::4:<br>1741686-1741698::ref | GACCGTGTCCTTACCGTGACG<br>TCCACCGACGTAAAGGCGACA<br>CAGGAGGAGAACCGGGAGCTG<br>AGGAGCAGGTGTGAGGAGCTC<br>CACGGGAAGAACCTGGAACTG<br>GGGAAGATCATGGAC<br>(SEQ ID NO: 1) | 30 bp |
| Fusion::FGFR3::4:<br>1808602-1808661::4:<br>1741429-1741488::ref | CCCACCTTCAAGCAGCTGGTG<br>GAGGACCTGGACCGTGTCCTT<br>ACCGTGACGTCCACCGACGTA<br>AAGGCGACACAGGAGGAGAAC<br>CGGGAGCTGAGGAGCAGGTGT<br>GAGGAGCTCCACGGG<br>(SEQ ID NO: 2) | 60 bp |
| Fusion::FGFR3::4:<br>1808572-1808661::4:<br>1741429-1741458::ref | GAGTGCTGGCATGCCGCGCCC<br>TCCCAGAGGCCCACCTTCAAG<br>CAGCTGGTGGAGGACCTGGAC<br>CGTGTCCTTACCGTGACGTCC<br>ACCGACGTAAAGGCGACACAG<br>GAGGAGAACCGGGAG<br>(SEQ ID NO: 3) | 90 bp | b) universal proe (O bp probe) (FIG. 2B):

| Probe name | Sequence |
| --- | --- |
| FGFR3::NM_000142::<br>17-TACC3::<br>NM_006342::11::<br>fbp0 | TGCACACACGACCTGTACATGATCATGCGGG<br>AGTGCTGGCATGCCGCGCCCTCCCAGAGGCC<br>CACCTTCAAGCAGCTGGTGGAGGACCTGGAC<br>CGTGTCCTTACCGTGACGTCCACCGAC<br>(SEQ ID NO: 4) | c) specific probe with overlap of 50 bp to a secondary fusion partner (FIG. 2C):

| Probe name | Sequence |
| --- | --- |
| FGFR3::NM_000142::<br>17-TACC3::<br>NM_006342::11::<br>fbp50 | CTCCCAGAGGCCCACCTTCAAGCAGCTGGTG<br>GAGGACCTGGACCGTGTCCTTACCGTGACGT<br>CCACCGACGTAAAGGCGACACAGGAGGAGAA<br>CCGGGAGCTGAGGAGCAGGTGTGAGGA<br>(SEQ ID NO: 5) | d) probes mix with universal probe (0 bp probe) and specific probes with overlap of 10 bp, 20 bp, 30 bp and 40 bp to secondary fusion partner (FIG. 2D):

| Probe name | Sequence |
| --- | --- |
| FGFR3::NM_000142::<br>17-TACC3:: | TGCACACACGACCTGTACATGATCATGCGG<br>GAGTGCTGGCATGCCGCGCCCTCCCAGAGG |

| Probe name | Sequence |
| --- | --- |
| NM_006342::11::<br>fbp0 | CCCACCTTCAAGCAGCTGGTGGAGGACCTG<br>GACCGTGTCCTTACCGTGACGTCCACCGAC<br>(SEQ ID NO: 4) |
| FGFR3::NM_000142::<br>17-TACC3::<br>NM_006342::11::<br>fbp10 | ACCTGTACATGATCATGCGGGAGTGCTGGC<br>ATGCCGCGCCCTCCCAGAGGCCCACCTTCA<br>AGCAGCTGGTGGAGGACCTGGACCGTGTCC<br>TTACCGTGACGTCCACCGACGTAAAGGCGA<br>(SEQ ID NO: 6) |
| FGFR3::NM_000142::<br>17-TACC3::<br>NM_006342::11::<br>fbp20 | GATCATGCGGGAGTGCTGGCATGCCGCGCC<br>CTCCCAGAGGCCCACCTTCAAGCAGCTGGT<br>GGAGGACCTGGACCGTGTCCTTACCGTGAC<br>GTCCACCGACGTAAAGGCGACACAGGAGGA<br>(SEQ ID NO: 7) |
| FGFR3::NM_000142::<br>17-TACC3::<br>NM_006342::11::<br>fbp30 | GAGTGCTGGCATGCCGCGCCCTCCCAGAGG<br>CCCACCTTCAAGCAGCTGGTGGAGGACCTG<br>GACCGTGTCCTTACCGTGACGTCCACCGAC<br>GTAAAGGCGACACAGGAGGAGAACCGGGAG<br>(SEQ ID NO: 8) |
| FGFR3::NM_000142::<br>17-TACC3::<br>NM_006342::11::<br>fbp40 | ATGCCGCGCCCTCCCAGAGGCCCACCTTCA<br>AGCAGCTGGTGGAGGACCTGGACCGTGTCC<br>TTACCGTGACGTCCACCGACGTAAAGGCGA<br>CACAGGAGGAGAACCGGGAGCTGAGGAGCA<br>(SEQ ID NO: 9) |

The analysis of heatmap of fragments that starts relative to fusion breakpoint for FGFR3-TACC3 fusion captured with high overlap probes (FIG. 2A) shows that these probes capture too many reads of WT secondary partner. About 60% of fragments around the fusion can be attributed to the secondary partner (TACC3) wild type transcript. Addition of the low overlap probes (30 bp) to the mix of high overlap probes does not reduce reads of WT secondary partner.

Figure 2A:
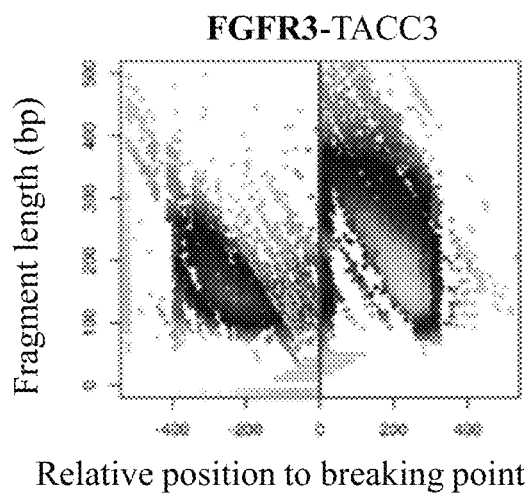
FIGS. 2A-2D shows heatmap of FGFR3-TACC3 fusion fragments that start relative to fusion breakpoint (0 bp position) detected with high overlap probes (FIG. 2A) as compared to those detected with low overlap probes (FIG. 2B-D) according to Example 2.
Figure 2B:
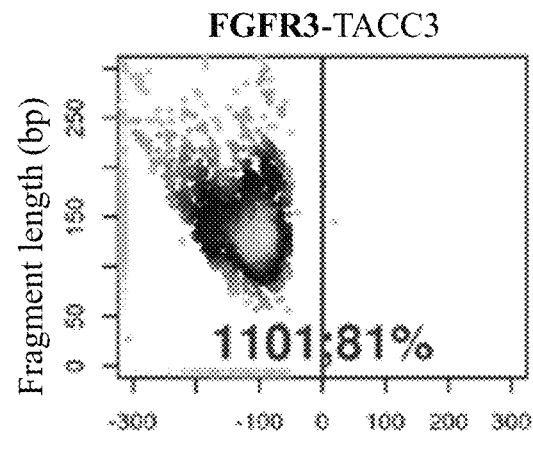
Figure 2C:
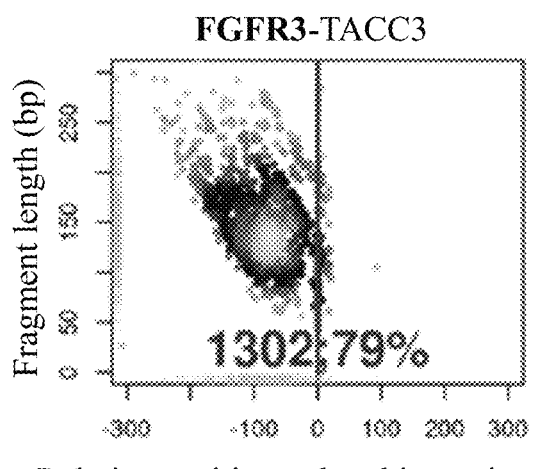
Figure 2D:
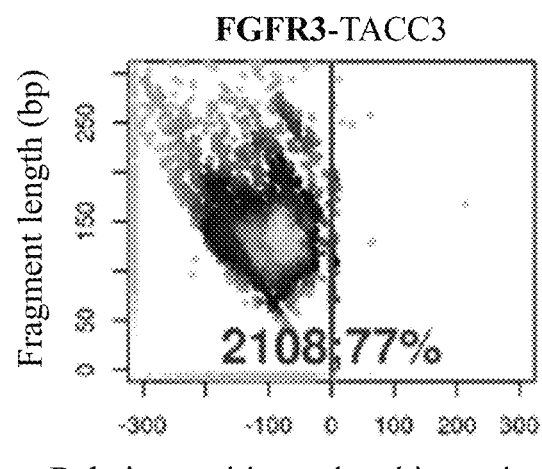

The analysis of heatmap of fragments that starts relative to fusion breakpoint for FGFR3-TACC3 fusion captured with low overlap probes (FIG. 2B, C, D) shows that these probes capture mainly secondary partner reads belonging to the targeted fusion. Advantageously, mix of probes could capture more fusion fragments than 0 bp and 50 bp probes alone (i.e., mix of probes—2108 fragments (FIG. 2D); 0 bp-1101 fragments (FIG. 2B); 50 bp-1302 fragments (FIG. 2C)). Only a mix of low overlap probes (FIG. 2D) allows to reduce reads of WT secondary partner as compared to reads obtained using high overlap probes (FIG. 2A). Advantageously, this mix of low overlap probes comprising a universal probe and specific low overlap probes allows for detection of known and novel fusion gene partners.

These results demonstrate that low overlap probes capture mainly secondary partner reads belonging to the targeted fusion and that advantageously mix of low overlap probes capture more fusion fragments than 0 bp and 50 bp probes alone. Only a mix of low overlap probes allows to reduce reads of WT secondary partner as compared to reads obtained using high overlap probes. Therefore, the design of fusion specific probes to capture known fusions/breakpoints has been optimized so that to avoid capturing the WT secondary partner counterpart.

Example 3: Comparison of Performance Between High Overlap Probe Design and Low Overlap Probe Design in Detection of PAX8-PPARG Fusion High overlap and low overlap probes performance was compared in detection of PAX8-PPARG fusion. PPARG is the primary fusion gene.

Material and Methods as in Example 2

The probes were designed according to the invention with a mix of probes containing high overlap probes mix (60 bp, 90 bp) with low overlap probes (30 bp) (FIG. 3A), or low overlap probes: 0 bp probes (FIG. 3B), or low overlap 50 bp probes (FIG. 3C), or a mix of 0 bp, 10 bp, 20 bp, 30 bp, and 40 bp low overlap probes (FIG. 3D), and including probes that target the PAX8-PPARG fusion. In this fusion gene PPARG is the primary fusion gene and PAX8 is the secondary fusion gene. The mix of probes contained probes targeting different gene fusions, for clarity only probes that target the PAX8-PPARG fusion are described and results of detection of the PAX8-PPARG fusion are reported.

The following probes were used:

a) a mix of high overlap probes (60 bp and 90 bp) and low overlap probes (30 bp) (FIG. 3A):

| Probe name | Probe sequence | type |
|---|---|---|
| Fusion: PPARG::2:<br>113992971-113993000::3:<br>12421203-12421292::ref | GGCAGTTCACGGGCCAGGCC<br>CTCCTCTCAGAAATGACCAT<br>GGTTGACACAGAGATGCCAT<br>TCTGGCCCACCAACTTTGGG<br>ATCAGCTCCGTGGATCTCTC<br>CGTAATGGAAGACCACTCCC<br>(SEQ ID NO: 10) | 90 bp |
| Fusion: PPARG::2:<br>113992971-113993030::3:<br>12421203-12421292::ref | ATGCCTTTCCCCATGCTGCC<br>TCCGTGTACGGGCAGTTCAC<br>GGGCCAGGCCCTCCTCTCAG<br>AAATGACCATGGTTGACACA<br>GAGATGCCATTCTGGCCCAC<br>CAACTTTGGGATCAGCTCCG<br>(SEQ ID NO: 11) | 60 bp |
| Fusion: PPARG::2:<br>113992971-113993060::3:<br>12421203-12421292::ref | AGCAAGTCGGCTCCGGGGTC<br>CCGCCCTTCAATGCCTTTCC<br>CCATGCTGCCTCCGTGTACG<br>GGCAGTTCACGGGCCAGGCC<br>CTCCTCTCAGAAATGACCAT<br>GGTTGACACAGAGATGCCAT<br>(SEQ ID NO: 12) | 30 bp | b) universal probe (0 bp probe) (FIG. 3D):

| Probe name | Sequence |
|---|---|
| PAX8::NM_003466::<br>9-PPARG::<br>NM_005037::2::<br>fbp0 | AAATGACCATGGTTGACACAGAGATGCCATTC<br>TGGCCCACCAACTTTGGGATCAGCTCCGTGGA<br>TCTCTCCGTAATGGAAGACCACTCCCACTCCT<br>TTGATATCAAGCCCTTCACTACTG<br>(SEQ ID NO: 13) | c) specific probe with overlap of 50 bp to secondary fusion partner (FIG. 3C):

| Probe name | Sequence |
|---|---|
| PAX8::NM_003466::<br>9-PPARG::<br>NM_005037::2::<br>fbp50 | CATGCTGCCTCCGTGTACGGGCAGTTCACGGG<br>CCAGGCCCTCCTCTCAGAAATGACCATGGTTG<br>ACACAGAGATGCCATTCTGGCCCACCAACTTT<br>GGGATCAGCTCCGTGGATCTCTCC<br>(SEQ ID NO: 14) | d) probes mix with universal probe (0 bp probe) and specific probes with overlap of 10 bp, 20 bp, 30 bp and 40 bp to secondary fusion partner (FIG. 3D):

| Probe name | Sequence |
|---|---|
| PAX8::NM_003466::<br>9-PPARG::<br>NM_005037::2::<br>fbp0 | AAATGACCATGGTTGACACAGAGATGCCATTC<br>TGGCCCACCAACTTTGGGATCAGCTCCGTGGA<br>TCTCTCCGTAATGGAAGACCACTCCCACTCCT<br>TTGATATCAAGCCCTTCACTACTG<br>(SEQ ID NO: 13) |
| PAX8::NM_003466::<br>9-PPARG::<br>NM_005037::2::<br>fbp10 | TCCTCTCAGAAATGACCATGGTTGACACAGAG<br>ATGCCATTCTGGCCCACCAACTTTGGGATCAG<br>CTCCGTGGATCTCTCCGTAATGGAAGACCACT<br>CCCACTCCTTTGATATCAAGCCCT<br>(SEQ ID NO: 15) |
| PAX8::NM_003466::<br>9-PPARG::<br>NM_005037::2::<br>fbp20 | GGCCAGGCCCTCCTCTCAGAAATGACCATGGT<br>TGACACAGAGATGCCATTCTGGCCCACCAACT<br>TTGGGATCAGCTCCGTGGATCTCTCCGTAATG<br>GAAGACCACTCCCACTCCTTTGAT<br>(SEQ ID NO: 16) |
| PAX8::NM_003466::<br>9-PPARG::<br>NM_005037::2::<br>fbp30 | GCAGTTCACGGGCCAGGCCCTCCTCTCAGAAA<br>TGACCATGGTTGACACAGAGATGCCATTCTGG<br>CCCACCAACTTTGGGATCAGCTCCGTGGATCT<br>CTCCGTAATGGAAGACCACTCCCA<br>(SEQ ID NO: 17) |
| PAX8::NM_003466::<br>9-PPARG::<br>NM_005037::2::<br>fbp40 | CCGTGTACGGGCAGTTCACGGGCCAGGCCCTC<br>CTCTCAGAAATGACCATGGTTGACACAGAGAT<br>GCCATTCTGGCCCACCAACTTTGGGATCAGCT<br>CCGTGGATCTCTCCGTAATGGAAG<br>(SEQ ID NO: 18) |

The analysis of heatmap of fragments that starts relative to fusion break-point for PAX8-PPARG fusion captured with high overlap probes (FIG. 3A) shows that these probes capture too many reads of WT secondary partner. About 39% of fragments around the fusion can be attributed to the secondary partner (PAX8) wild type transcript. Addition of the low overlap probes (30 bp) to the mix of high overlap probes does not reduce reads of WT secondary partner.

Figure 3A:
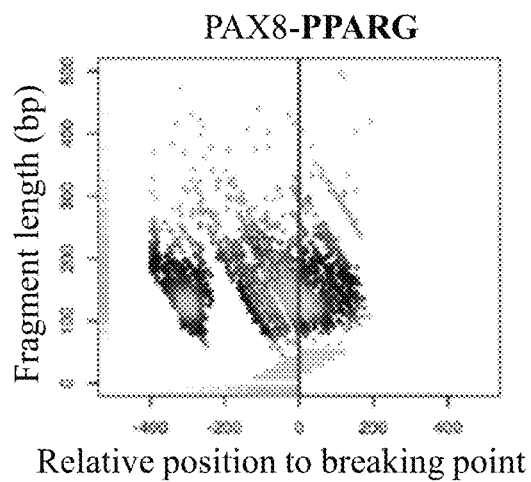
FIGS. 3A-3D shows heatmap of PAX8-PPARG fusion fragments that starts relative to fusion breakpoint (0 bp position) detected with high overlap probes (FIG. 3A) as compared to those detected with low overlap probes (FIG. 3B-D) according to Example 3.
Figure 3B:
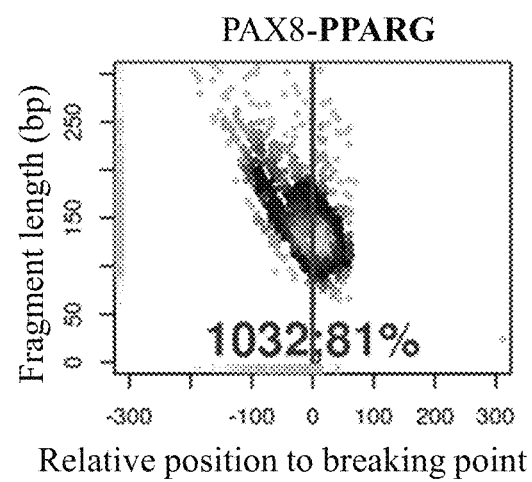
Figure 3C:
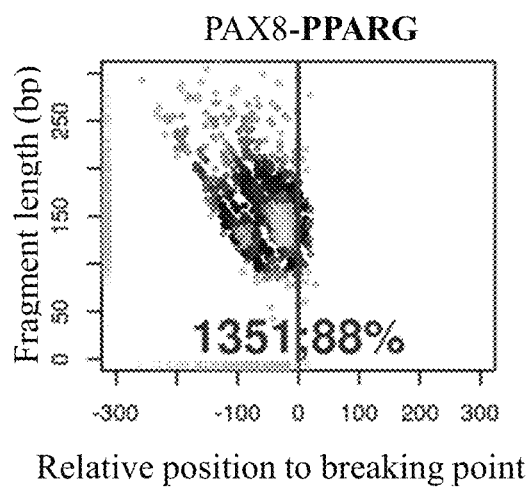
Figure 3D:
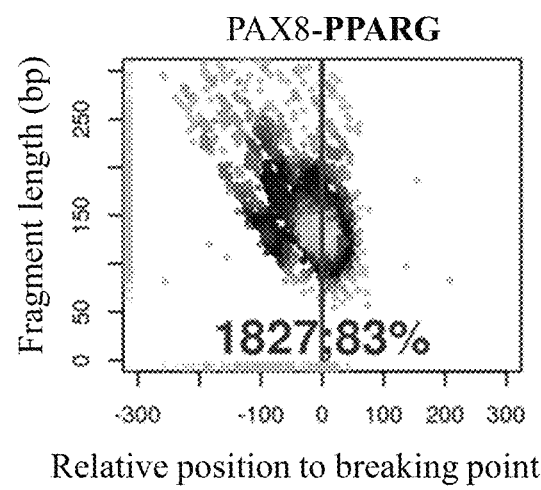

The analysis of heatmap of fragments that starts relative to fusion break-point for PAX8-PPARG fusion captured with low overlap probes (FIG. 31D, C, D) shows that these probes capture mainly secondary partner reads belonging to the targeted fusion. Advantageously, mix of probes could capture more fusion fragments than 0 bp and 50 bp probes alone (i.e., mix of probes-1827 fragments (FIG. 3D): 0 bp-1032 fragments (FIG. 3B). 50 bp-1351 fragments (FIG. 3C)). Only a mix of low overlap probes (FIG. 3D) allows to reduce reads of WT secondary partner as compared to reads obtained using high overlap probes (FIG. 3A). Advantageously, this mix of low overlap probes comprising a universal probe and specific low overlap probes allows for detection of known and novel fusion gene partners.

These results demonstrate that low overlap probes capture mainly secondary partner reads belonging to the targeted fusion and that advantageously mix of low overlap probes capture more fusion fragments than 0 bp and 50 bp probes alone. Only a mix of low overlap probes allows to reduce reads of WT secondary partner as compared to reads obtained using high overlap probes. Therefore, the design of fusion specific probes to capture known fusions/breakpoints has been optimized so that to avoid capturing the WT secondary partner counterpart.

Example 4: Capture with Low Overlap Probes of Different Fusions in Clinical and Reference Samples Number of fused fragments captured with low overlap probe design for different fusions in clinical and reference samples were compared as described.

Material and Methods

RNA-seq libraries were prepared using 100 ng of RNA extracted from clinical FFPE or reference (Seraseq® FFPE Tumor Fusion RNA v2 reference material) samples. Individually barcoded whole-transcriptome libraries were then captured using the xGEN Lockdown IDT® probe-based capture technology using custom panels. The probes were designed according to the invention with a mix of probes containing low overlap probes 0 bp probes (0 bp), or a mix of 0 bp, 10 bp, 20 bp, 30 bp, 40 bp, and 50 bp low overlap probes (mix), or a mix of 0 bp and 50 bp low overlap probes (0+50 bp). Captured libraries were then sequenced using an Illumina MiSeq instrument. Data were analyzed by mapping the reads with BWA-MEM aligner to a home-made fusion synthetic genome and heatmap of fragments starts relative to fusion breakpoint were generated. Fusions were detected in both clinical samples (solid tumors; sample 1 and 2 contained confirmed CD74-ROS1 fusions and sample 3 contained a confirmed EML4-ALK fusion (S1, S2 and S3 respectively) and reference material (RS; seracare) containing 14 different fusions and 2 exon-skipping events. Different fusions were targeted, including EML4-ALK, KIF5B-RET, NCOA4-RET, SLC34A2-ROS1, TPM3-NTRK1, FGFR3-BAIAP2L1, PAX8-PPARG, FGFR3-TACC3, ETV6-NTRK3, LMNA-NTRK1, and SLC45A3-BRAF.

Figure 4:
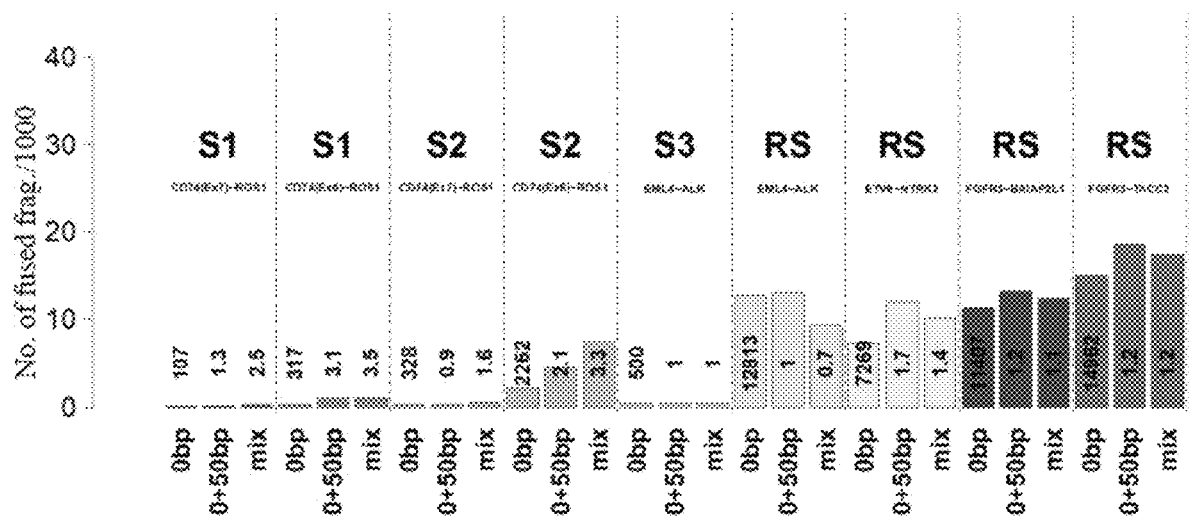
FIG. 4 Bars plot shows number of fragments spanning the breakpoint (divided by 1000) captured with low overlap probe design (0 bp or 0+50 bp or mix (0 bp+10 bp+20 bp+30 bp+40 bp+50 bp)) for different fusions in clinical samples (S1, S2, S3) and reference sample (RS: Seraseq® FFPE Tumor Fusion RNA v2) as described in Example 4. Number of detected fused fragments is reported as well as number of fused fragments in condition 0 bp, the fold-change of fused fragments in condition 0+50 bp as compared to 0 bp, the fold-change of fused fragments in condition 'mix' as compared to 0 bp (noted over the respective bars).
Figure 4:
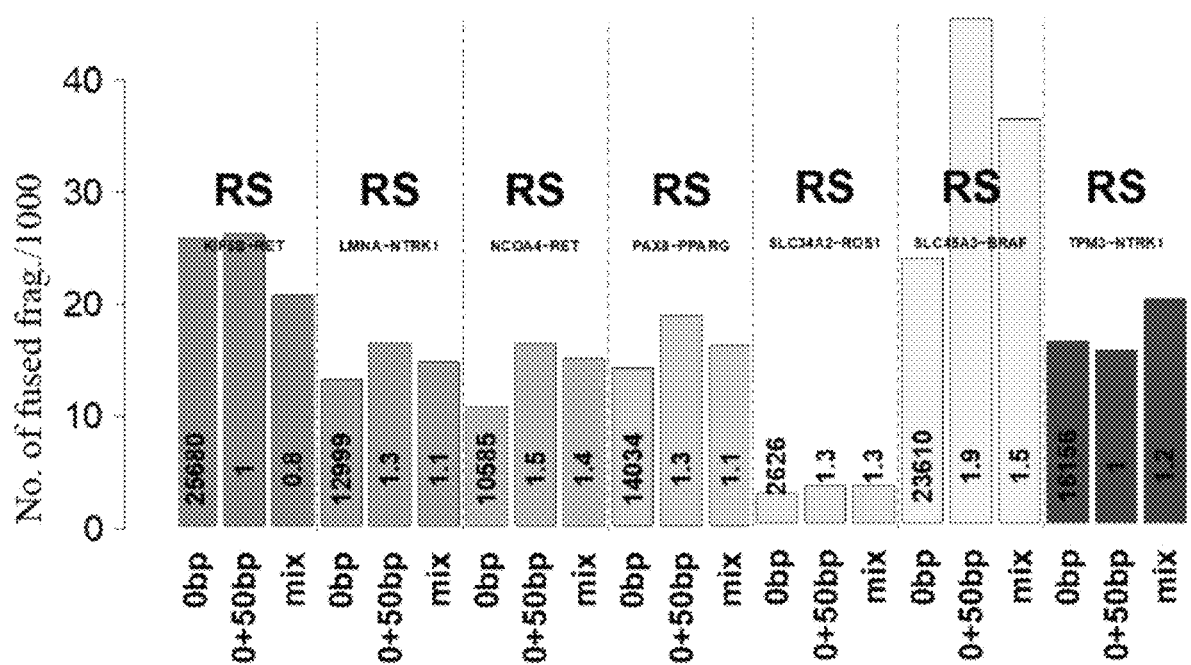

Number of detected fused fragments are reported as well as number of fused fragments in condition 0 bp, the fold-change of fused fragments in condition 0+50 bp compared to 0 bp, and the fold-change of fused fragments in condition mix compared to 0 bp (FIG. 4).

The Following Probes were Used:
a) universal probe (0 bp probe):

| Probe name | probe sequence |
|---|---|
| CD74::NM_004355:<br>6-ROS1::NM_002944::34::<br>fbp0 | ATGATTTTTGGATACCAGAAACAAGT<br>TTCATACTTACTATTATAGTTGGAAT<br>ATTTCTGGTTGTTACAATCCCACTGA<br>CCTTTGTCTGGCATAGAAGATTAAAG<br>AATCAAAAAAGTGCCA<br>(SEQ ID NO: 19) |
| EML4::NM_019063::<br>13-ALK::NM_004304::20::<br>fbp0 | TGTACCGCCGGAAGCACCAGGAGCTG<br>CAAGCCATGCAGATGGAGCTGCAGAG<br>CCCTGAGTACAAGCTGAGCAAGCTCC<br>GCACCTCGACCATCATGACCGACTAC<br>AACCCCAACTACTGCT<br>(SEQ ID NO: 20) |
| ETV6::NM_001987::<br>5-NTRK3::NM_002530::<br>15::fbp0 | ATGTGCAGCACATTAAGAGGAGAGAC<br>ATCGTGCTGAAGCGAGAACTGGGTGA<br>GGGAGCCTTTGGAAAGGTCTTCCTGG<br>CCGAGTGCTACAACCTCAGCCCGACC<br>AAGGACAAGATGCTTG<br>(SEQ ID NO: 21) |
| FGFR3::NM_000142::<br>17-TACC3::NM_006342::<br>11::fbp0 | TGCACACACGACCTGTACATGATCAT<br>GCGGGAGTGCTGGCATGCCGCGCCCT<br>CCCAGAGGCCCACCTTCAAGCAGCTG<br>GTGGAGGACCTGGACCGTGTCCTTAC<br>CGTGACGTCCACCGAC<br>(SEQ ID NO: 4) |
| LMNA::NM_005572::<br>2-NTRK1::NM_002529::<br>11::fbp0 | GTCTCGGTGGCTGTGGGCCTGGCCGT<br>CTTTGCCTGCCTCTTCCTTTCTACGC<br>TGCTCCTTGTGCTCAACAAATGTGGA<br>CGGAGAAACAAGTTTGGGATCAACCG<br>CCCGGCTGTGCTGGCT<br>(SEQ ID NO: 22) |
| TPM3::NM_152263::<br>8-NTRK1::NM_002529::<br>10::fbp0 | ACACTAACAGCACATCTGGAGACCCG<br>GTGGAGAAGAAGGACGAAACACCTTT<br>TGGGGTCTCGGTGGCTGTGGGCCTGG |
| | CCGTCTTTGCCTGCCTCTTCCTTTCT<br>ACGCTGCTCCTTGTGC<br>(SEQ ID NO: 23) |
| FGFR3::NM_000142::<br>17-BAIAP2L1::<br>NM_018842::2::fbp0 | TGCACACACGACCTGTACATGATCAT<br>GCGGGAGTGCTGGCATGCCGCGCCCT<br>CCCAGAGGCCCACCTTCAAGCAGCTG<br>GTGGAGGACCTGGACCGTGTCCTTAC<br>CGTGACGTCCACCGAC<br>(SEQ ID NO: 4) |
| KIF5B::NM_004521::<br>24-RET::NM_020630::<br>11::fbp0 | ATCCACTGTGCGACGAGCTGTGCCGC<br>ACGGTGATCGCAGCCGCTGTCCTCTT<br>CTCCTTCATCGTCTCGGTGCTGCTGT<br>CTGCCTTCTGCATCCACTGCTACCAC<br>AAGTTTGCCCACAAGC<br>(SEQ ID NO: 24) |
| MCOA4::NM_005437::<br>7-RET::NM_020630::<br>12::fbp0 | GAGGATCCAAAGTGGGAATTCCCTCG<br>GAAGAACTTGGTTCTTGGAAAAACTC<br>TAGGAGAAGGCGAATTTGGAAAAGTG<br>GTCAAGGCAACGGCCTTCCATCTGAA<br>AGGCAGAGCAGGGTAC<br>(SEQ ID NO: 25) |
| PAX8::NM_003466::<br>9-PPARG::NM_005037::<br>2::fbp0 | AAATGACCATGGTTGACACAGAGATG<br>CCATTCTGGCCCACCAACTTTGGGAT<br>CAGCTCCGTGGATCTCTCCGTAATGG<br>AAGACCACTCCCACTCCTTTGATATC<br>AAGCCCTTCACTCTG<br>(SEQ ID NO: 13) |
| SLC24A2::NM_0006424::<br>4-ROS1::NM_002944::<br>34::fbp0 | ATGATTTTTGGATACCAGAAACAAGT<br>TTCATACTTACTATTATAGTTGGAAT<br>ATTTCTGGTTGTTACAATCCCACTGA<br>CCTTTGTCTGGCATAGAAGATTAAAG<br>AATCAAAAAAGTGCCA<br>(SEQ ID NO: 19) |
| SLC34A3::NM_033102::<br>1-BRAF::NM_004333::<br>8::fbp0 | GCCCCAAATTCTCACCAGTCCGTCTC<br>CTTCAAAATCCATTCCAATTCCACAG<br>CCCTTCCGACCAGCAGATGAAGATCA<br>TCGAAATCAATTTGGGCAACGAGACC<br>GATCCTCATCAGCTCC<br>(SEQ ID NO: 26) | b) probes mix with a universal probe (0 bp probe) and a specific probe with overlap of 50 bp to secondary fusion partner (0+50 bp):

| Probe name | probe sequence |
|---|---|
| CD74::NM_004355::<br>6-ROS1::NM_002944::<br>34::fbp0 | ATGATTTTTGGATACCAGAAACAAGTTTC<br>ATACTTACTATTATAGTTGGAATATTTCT<br>GGTTGTTACAATCCCACTGACCTTTGTCT<br>GGCATAGAAGATTAAAGAATCAAAAAAGT<br>GCCA<br>(SEQ ID NO: 19) |
| EML4::NM_019063::<br>13-ALK::NM_004304::<br>20::fbp0 | TGTACCGCCGGAAGCACCAGGAGCTGCAA<br>GCCATGCAGATGGAGCTGCAGAGCCCTGA<br>GTACAAGCTGAGCAAGCTCCGCACCTCGA<br>CCATCATGACCGACTACAACCCCAACTAC<br>TGCT<br>(SEQ ID NO: 20) |
| ETV6::NM_001987::<br>5-NTRK3::<br>NM_002530::15::fbp0 | ATGTGCAGCACATTAAGAGGAGAGACATC<br>GTGCTGAAGCGAGAACTGGGTGAGGGAGC<br>CTTTGGAAAGGTCTTCCTGGCCGAGTGCT<br>ACAACCTCAGCCCGACCAAGGACAAGATG<br>CTTG<br>(SEQ ID NO: 21) |
| FGFR3::NM_000142::<br>17-TACC3:: | TGCACACACGACCTGTACATGATCATGCG<br>GGAGTGCTGGCATGCCGCGCCCTCCCAGA |

-continued

| Probe name | probe sequence |
|---|---|
| NM_006342::11::fbp0 | GGCCCACCTTCAAGCAGCTGGTGGAGGAC CTGGACCGTGTCCTTACCGTGACGTCCAC CGAC (SEQ ID NO: 4) |
| LMNA::NM_005572::2-NTRK1::NM_002529::11::fbp0 | GTCTCGGTGGCTGTGGGCCTGGCCGTCTT TGCCTGCCTCTTCCTTTCTACGCTGCTCC TTGTGCTCAACAAATGTGGACGGAGAAAC AAGTTTGGGATCAACCGCCCGGCTGTGCT GGCT (SEQ ID NO: 22) |
| TPM3::NM_152263::8-NTRK1::NM_002529::10::fbp0 | ACACTAACAGCACATCTGGAGACCCGGTG GAGAAGAAGGACGAAACACCTTTTGGGGT CTCGGTGGCTGTGGGCCTGGCCGTCTTTG CCTGCCTCTTCCTTTCTACGCTGCTCCTT GTGC (SEQ ID NO: 23) |
| FGFR3::NM_000142::17-BAIAP2L1::NM_018842::2::fbp0 | TGCACACACGACCTGTACATGATCATGCG GGAGTGCTGGCATGCCGCGCCCTCCCAGA GGCCCACCTTCAAGCAGCTGGTGGAGGAC CTGGACCGTGTCCTTACCGTGACGTCCAC CGAC (SEQ ID NO: 4) |
| KIF5B::NM_004521::24-RET::NM_020630::11::fbp0 | ATCCACTGTGCGACGAGCTGTGCCGCACG GTGATCGCAGCCGCTGTCCTCTTCCTTCT CATCGTCTCGGTGCTGCTGTCTGCCTTCT GCATCCACTGCTACCACAAGTTTGCCCAC AAGC (SEQ ID NO: 24) |
| NCOA4::NM_005437::7-RET::NM_020630::12::fbp0 | GAGGATCCAAAGTGGGAATTCCCTCGGAA GAACTTGGTTCTTGGAAAAACTCTAGGAG AAGGCGAATTTGGAAAAGTGGTCAAGGCA ACGGCCTTCCATCTGAAAGGCAGAGCAGG GTAC (SEQ ID NO: 25) |
| PAX8::NM_003466::9-PPARG::NM_005037::2::fbp0 | AAATGACCATGGFTGACACAGAGATGCCA TTCTGGCCCACCAACTTTGGGATCAGCTC CGTGGATCTCTCCGTAATGGAAGACCACT CCCACTCCTTTGATATCAAGCCCTTCACT ACTG (SEQ ID NO: 13) |
| SLC34A2::NM_006424::4-ROS1::NM_002944::34::fbp0 | ATGATTTTTGGATACCAGAAACAAGTTTC ATACTTACTATTATAGTTGGAATATTTCT GGTTGTTACAATCCCACTGACCTTTGTCT GGCATAGAAGATTAAAGAATCAAAAAAGT GCCA (SEQ ID NO: 19) |
| SLC45A3::NM_033102::1-BRAF::NM_004333::8::fbp0 | GCCCCAAATTCTCACCAGTCCGTCTCCTT CAAAATCCATTCCAATTCCACAGCCCTTC CGACCAGCAGATGAAGATCATCGAAATCA ATTTGGGCAACGAGACCGATCCTCATCAG CTCC (SEQ ID NO: 26) |
| CD74::NM_004355::6-ROS1::NM_002944::34::fbp50 | ATGAGCAGGCACTCCTTGGAGCAAAAGCC CACTGACGCTCCACCGAAAGATGATTTTT GGATACCAGAAACAAGTTTCATACTTACT ATTATAGTTGGAATATTTCTGGTTGTTAC AATC (SEQ ID NO: 27) |
| EML4::NM_019603::13-ALK::NM_004304::20::fbp50 | ATATGGAGCAAAACTACTGTAGAGCCCAC ACCTGGGAAAGGACCTAAAGTGTACCGCC GGAACACCAGGAGCTGCAAGCCATGCAG ATGGAGCTGCAGAGCCCTGAGTACAAGCT GAGC (SEQ ID NO: 28) |
| ETV6::NM_001987::5-NTRK3:: | TCTGTCTCCCCGCCTGAAGAGCACGCCAT GCCCATTGGGAGAATAGCAGATGTGCAGC |
| NM_002530::15::fbp50 | ACATTAAGAGGAGAGACATCGTGCTGAAG CGAGAACTGGGTGAGGGAGCCTTTGGAAA GGTC (SEQ ID NO: 29) |
| FGFR3::NM_000142::17-TACC3::NM_006342::11::fbp50 | CTCCCAGAGGCCCACCTTCAAGCAGCTGG TGGAGGACCTGGACCGTGTCCTTACCGTG ACGTCCACCGACGTAAAGGCGACACAGGA GGAGAACCGGGAGCTGAGGAGCAGGTGTG AGGA (SEQ ID NO: 5) |
| LMNA::NM_005572::2-NTRK1::NM_002529::11::fbp50 | GCGCACGCTGGAGGGCGAGCTGCATGATC TGCGGGGCCAGGTGGCCAAGGTCTCGGTG GCTGTGGGCCTGGCCGTCTTTGCCTGCCT CTTCCTTTCTACGCTGCTCCTTGTGCTCA ACAA (SEQ ID NO: 30) |
| TPM3::NM_152263::8-NTRK1::NM_002529::10::fbp50 | AGATAAATATGAGGAAGAAATCAAGATTC TTACTGATAAACTCAAGGAGACACTAACA GCACATCTGGAGACCCGGTGGAGAAGAAG GACGAAACACCTTTTGGGGTCTCGGTGGC TGTG (SEQ ID NO: 31) |
| FGFR3::NM_000142::17-BAIAP2L1::NM_018842::2::fbp50 | CTCCCAGAGGCCCACCTTCAAGCAGCTGG TGGAGGACCTGGACCGTGTCCTTACCGTG ACGTCCACCGACAATGTTATGGAACAGTT CAATCCTGGGCTGCGAAATTTAATAAACC TGGG (SEQ ID NO: 32) |
| KIF5B::NM_004521::24-RET::NM_020630::11::fbp50 | GCAGTCAGGTCAAAGAATATGGCCAGAAG AGGGCATTCTGCACAGATTGATCCACTGT GCGACGAGCTGTGCCGCACGGTGATCGCA GCCGCTGTCCTCTTCCTTCATCGTCTC GGTG (SEQ ID NO: 33) |
| NCOA4::NM_005437::7-RET::NM_020630::12::fbp50 | CGACCCCCAGGACTGGCTTACCCAAAAGC AGACCTTGGAGAACAGTCAGGAGGATCCA AAGTGGGAATTCCCTCGGAAGAACTTGGT TCTTGGAAAAACTCTAGGAGAAGGCGAAT TTGG (SEQ ID NO: 34) |
| PAX8::NM_033466::9-PPARG::NM_005037::2::fbp50 | CATGCTGCCTCCGTGTACGGGCAGTTCAC GGGCCAGGCCCTCCTCTCAGAAATGACCA TGGTTGACACAGAGATGCCATTCTGGCCC ACCAACTTTGGGATCAGCTCCGTGGATCT CTCC (SEQ ID NO: 14) |
| SLC34A2::NM_006424::4-ROS1::NM_002944::34::fbp50 | TTCGTGTGCTCCCTGGATATTCTTAGTAG CGCCTTCCAGCTGGTTGGAGATGATTTTT GGATACCAGAAACAAGTTTCATACTTACT ATTATAGTTGGAATATTTCTGGTTGTTAC AATC (SEQ ID NO: 35) |
| SLC45A3::NM_033102::1-BRAF::NM_004333::8::fbp50 | ACCAGCCTGCACGCGCTGGCTCCGGGTGA CAGCCGCGCGCCTCGGCCAGGCCCCAAAT TCTCACCAGTCCGTCTCCTTCAAAATCCA TTCCAATTCCACAGCCCTTCCGACCAGCA GATG (SEQ ID NO: 36) | c) probes mix with a universal probe (0 bp probe) and specific probes with overlap of 10 bp, 20 bp, 30 bp, 40 bp, 50 bp to secondary fusion partner (mix):

| Probe name | probe sequence |
|---|---|
| CD74::NM_004355::6-ROS1::NM_002944::34::fbp0 | ATGATTTTGGATACCAGAAACAAGTTTCATACTTACTATTATAGTTGGAA<br>TATTTCTGGTTGTTACAATCCCACTGACCTTTGTCTGGCATAGAAGATTAA<br>AGAATCAAAAAGTGCCA<br>(SEQ ID NO: 19) |
| EML4::NM_019063::13-ALK::NM_004304::20::fbp0 | TGTACCGCCGGAAGCACCAGGAGCTGCAAGCCATGCAGATGGAGCTGCAGA<br>GCCCTGAGTACAAGCTGAGCAAGCTCCGCACCTCGACCATCATGACCGACT<br>ACAACCCCAACTACTGCT<br>(SEQ ID NO: 20) |
| E1V6::NM_001987:5-NTRK3::NM_002530::15::fbp0 | ATGTGCAGCACATTAAGAGGAGAGACATCGTGCTGAAGCGAGAACTGGGTG<br>AGGGAGCCTTTGGAAAGGTCTTCCTGGCCGAGTGCTACAACCTCAGCCCGA<br>CCAAGGACAAGATGCTTG<br>(SEQ ID NO: 21) |
| FGFR3::NM_000142::17-TACC3::NM_006342::11::fbp0 | TGCACACACGACCTGTACATGATCATGCGGGAGTGCTGGCATGCCGCGCCC<br>TCCCAGAGGCCCACCTTCAAGCAGCTGGTGGAGGACCTGGACCGTGTCCTT<br>ACCGTGACGTCCACCGAC<br>(SEQ ID NO: 4) |
| LMNA::NM_005572::2-NTRK1::NM_002529::11::fp0 | GTCTCGGTGGCTGTGGGCCTGGCCGTCTTTGCCTGCCTCTTCCTTTCTACG<br>CTGCTCCTTGTGCTCAACAAATGTGGACGGAGAAACAAGTTTGGGATCAAC<br>CGCCCGGCTGTGCTGGCT<br>(SEQ ID NO: 22) |
| TPM3::NM_152263::8-NTRK1::NM_002529::10::fbp0 | ACACTAACAGCACATCTGGAGACCCGGTGGAGAAGAAGGACGAAACACCTT<br>TTGGGGGFCTCGGTGGCTGTGGGCCTGGCCGTCTTTGCCTGCCTCTTCCTTT<br>CTACGCTGCTCCTTGTGC<br>(SEQ ID NO: 23) |
| FGFR3::NM_000142::17-BAIAP2L1::NM_018842::2::fbp0 | TGCACACACGACCTGTACATGATCATGCGGGAGTGCTGGCATGCCGCGCCC<br>TCCCAGAGGCCCACCTTCAAGCAGCTGGTGGAGGACCTGGACCGTGTCCTT<br>ACCGTGACGTCCACCGAC<br>(SEQ ID NO: 4) |
| KIF5B::NM_004521::24-RET::NM_020630::11::fbpo | ATCCACTGTGCGACGAGCTGTGCCGCACGGTGATCGCAGCCGCTGTCCTCT<br>TCTCCTTCATCGTCTCGGTGCTGCTGTCTGCCTTCTGCATCCACTGCTACC<br>ACAAGTTTGCCCACAAGC<br>(SEQ ID NO: 24) |
| NCOA4::NM_005437::7-RET::NM_020630::12::fbp0 | GAGGATCCAAAGTGGGAATTCCCTCGGAAGAACTTGGTTCTTGGAAAAACT<br>CTAGGAGAAGGCGAATTTGGAAAAGTGGTCAAGGCAACGGCCTTCCATCTG<br>AAAGGCAGAGCAGGGTAC<br>(SEQ ID NO: 25) |
| PAX8::NM_003466::9-PPARG::NM_005037::2::fbp0 | AAATGACCATGGTTGACACAGAGATGCCATTCTGGCCCACCAACTTTGGGA<br>TCAGCTCCGTGGATCTCTCCGTAATGGAAGACCACTCCCACTCCTTTGATA<br>TCAAGCCCTTCACTACTG<br>(SEQ ID NO: 13) |
| SLC34A2::NM_006424::4-ROS1::NM_002944::34::fbp0 | ATGATTTTGGATACCAGAAACAAGTTTCATACTTACTATTATAGTTGGAA<br>TATTTCTGGTTGTTACAATCCCACTGACCTTTGTCTGGCATAGAAGATTAA<br>AGAATCAAAAAGTGCCA<br>(SEQ ID NO: 19) |
| SLC45A3::NM_033102::1-BRAF::NM_004333::8::fbp0 | GCCCAAATTCTCACCAGTCCGTCTCCTTCAAAATCCATTCCAATTCCACA<br>GCCCTTCCGACCAGCAGATGAAGATCATCGAAATCAATTTGGGCAACGAGA<br>CCGATCCTCATCAGCTCC<br>(SEQ ID NO: 26) |
| CD74::NM_004355::6-ROS1::NM_002944::34::fbp10 | CACCGAAAGATGATTTTGGATACCAGAAACAAGTTTCATACTTACTATTA<br>TAGTTGGAATATTTCTGGTTGTTACAATCCCACTGACCTTTGTCTGGCATA<br>GGAAGATTAAAGAATCAAA<br>(SEQ ID NO: 37) |
| EML4::NM_019063::13_ALK::NM_004304::20::fbp10 | GACCTAAAGTGTACCGCCGGAAGCACCAGGAGCTGCAAGCCATGCAGATGG<br>AGCTGCAGAGCCTGAGTACAAGCTGAGCAAGCTCCGCACCTCGACCATCAT<br>GACCGACTACAACCCCA<br>(SEQ ID NO: 38) |
| ETV6::NM_001987::5-NTRK3::NM_002530::15::fbp10 | GAATAGCAGATGTGCAGCACATTAAGAGGAGAGACATCGTGCTGAAGCGAG<br>AACTGGGTGAGGGAGCCTTTGGAAAGGTCTTCCTGGCCGAGTGCTACAACC<br>TCAGCCCGACCAAGGACA<br>(SEQ ID NO: 39) |
| FGFR3::NM_000142::17-TACC3::NM_006342::11::fbp10 | ACCTGTACATGATCATGCGGGAGTGCTGGCATGCCGCGCCCTCCCAGAGGC<br>CCACCTTCAAGCAGCTGGTGGAGGACCTGGACCGTGTCCTTACCGTGACGT<br>CCACCGACGTAAAGGCGA<br>(SEQ ID NO: 6) |

-continued

| Probe name | probe sequence |
|---|---|
| LMNA::NM_005572::2-<br>NTRK1::NM_002529::11::fp10 | GTGGCCAAGGTCTCGGTGGCTGTGGGCCTGGCCGTCTTTGCCTGCCTCTTC<br>CTTTCTACGCTGCTCCTTGTGCTCAACAAATGTGGACGGAGAAACAAGTTT<br>GGGATCAACCGCCCGGCT<br>(SEQ ID NO: 40) |
| TPMS::NM_152263::8-<br>NTRK1::NM_002529::10::fbp10 | ACCTGGAAGACACTAACAGCACATCTGGAGACCCGGTGGAGAAGAAGGACG<br>AAACACCTTTTGGGGTCTCGGTGGCTGTGGGCCTGGCCGTCTTTGCCTGCC<br>TCTTCCTTTCTACGCTGC<br>(SEQ ID NO: 41) |
| FGFR3::NM_000142::17-<br>BAIAP2L1::NM_018842::2::fbp10 | ACCTGTACATGATCATGCGGGAGTGCTGGCATGCCGCGCCCTCCCAGAGGC<br>CCACCTTCAAGCAGCTGGTGGAGGACCTGGACCGTGTCCTTACCGTGACGT<br>CCACCGACAATGTTATGG<br>(SEQ ID NO: 42) |
| KIF5B::NM_004521::24-<br>RET::NM_020630::11::fbp10 | CACAGATTGATCCACTGTGCGACGAGCTGTGCCGCACGGTGATCGCAGCCG<br>CTGTCCTCTTCTCCTTCATCGTCTCGGTGCTGCTGTCTGCCTTCTGCATCC<br>ACTGCTACCACAAGTTTG<br>(SEQ ID NO 43) |
| NCOA4::NM_005437::7-<br>RET::NM_020630::12::fbp10 | AACAGTCAGGAGGATCCAAAGTGGGAATTCCCTCGGAAGAACTTGGTTCTT<br>GGAAAAACTCTAGGAGAAGGCGAATTTGGAAAAGTGGTCAAGGCAACGGCC<br>TTCCATCTGAAAGGCAGA<br>(SEQ ID NO: 44) |
| PAX8::NM_003466::9-<br>PPARG::NM_005037::2::fbp10 | TCCTCTCAGAAATGACCATGGTTGACACAGAGATGCCATTCTGGCCCACCA<br>ACTTTGGGATCAGCTCCGTGGATCTCTCCGTAATGGAAGACCACTCCCACT<br>CCTTTGATATCAAGCCCT<br>(SEQ ID NO: 15) |
| SLC34A2::NM_006424::4-<br>ROS1::NM_002944::34::fbp10 | TGGTTGGAGATGATTTTTGGATACCAGAAACAAGTTTCATACTTACTATTA<br>TAGTTGGAATATTTCTGGTTGTTACAATCCCACTGACCTTTGTCTGGCATA<br>GAAGATTAAAGAATCAAA<br>(SEQ ID NO: 45) |
| SLC45A3::NM_033102::1-<br>BRAF::NM_004333::8::fbp10 | CTCGGCCAGGCCCCAAATTCTCACCAGTCCGTCTCCTTCAAAATCCATTCC<br>AATTCCACAGCCCTTCCGACCAGCAGATGAAGATCATCGAAATC<br>AATTTGGGCAACGAGACCGATCCTC<br>(SEQ ID NO: 46) |
| CD74::NM_004355::6-<br>ROS1::NM_002944::34::fbp20 | ACTGACGCTCCACCGAAAGATGATTTTGGATACCAGAAACAAGTTTCATAC<br>TTACTATTATAGTTGGAATATTTCTGGTTGTTACAATCCCACTGACCTTTG<br>TCTGGCATAGAAGATTA<br>(SEQ ID NO: 47) |
| EML4::NM_019063::13-<br>ALK::NM_004304::20::fbp20 | CCTGGGAAAGGACCTAAAGTGTACCGCCGGAAGCACCAGGAGCTGCAAGCC<br>ATGCAGATGGAGCTGCAGAGCCCTGAGTACAAGCTGAGCAAGCTCCGCACC<br>CTCGACCATCATGACCGAC<br>(SEQ ID NO: 48) |
| ETV6::NM_001987::5-<br>NTRK3::NM_002530::15::fbp20 | CCCATTGGGAGAATAGCAGATGTGCAGCACATTAAGAGGAGAGACATCGTG<br>CTGAAGCGAGAACTGGGTGAGGGAGCCTTTGGAAAGGTCTTCCTGGCCGAG<br>TGCTACAACCTCAGCCCG<br>(SEQ ID NO: 49) |
| FGFR3::NM_000142::17-<br>TACC3::NM_006342::11::fbp20 | GATCATGCGGGAGTGCTGGCATGCCGCGCCCTCCCAGAGGCCCACCTTCAA<br>GCAGCTGGTGGAGGACCTGGACCGTGTCCTTACCGTGACGTCCACCGACGT<br>AAAGGCGACACAGGAGGA<br>(SEQ ID NO: 7) |
| LMNA::NM_005572::2-<br>NTRK1::NM_002529::11:fbp20 | GCGGGGCCAGGTGGCCAAGGTCTCGGTGGCTGTGGGCCTGGCCGTCTTTGC<br>CTGCCTCTTCCTTTCTACGCTGCTCCTTGTGCTCAACAAATGTGGACGGAG<br>AAACAAGTTTGGGATCAA<br>(SEQ ID NO: 50) |
| TPM3::NM_152263::8-<br>NTRK1::NM_002529::10:fbp20 | ACAATTGATGACCTGGAAGACACTAACAGCACATCTGGAGACCCGGTGGAG<br>AAGAAGGACGAAACACCTTTTGGGGTCTCGGTGGCTGTGGGCCTGGCCGTC<br>TTTGCCTGCCTCTTCCTT<br>(SEQ ID NO: 51) |
| FGFR3::NM_000142::17-<br>BAIAP2L1::NM_018842::2::fbp20 | GATCATGCGGGAGTGCTGGCATGCCGCGCCCTCCCAGAGGCCCACCTTCAA<br>GCAGCTGGTGGAGGACCTGGACCGTGTCCTTACCGTGACGTCCACCGACAA<br>TGTTATGGAACAGTTCAA<br>(SEQ ID NO: 52) |

-continued

| Probe name | probe sequence |
| --- | --- |
| KIF5B::NM_004521::24-<br>RET::NM_020630::11::fbp20 | GGGCATTCTGCACAGATTGATCCACTGTGCGACGAGCTGTGCCGCACGGTG<br>ATCGCAGCCGCTGTCCTCTTCTCCTTCATCGTCTCGGTGCTGCTGTCTGCC<br>TTCTGCATCCACTGCTAC<br>(SEQ ID NO: 53) |
| NCOA4::NM_005437::7-<br>RET::NM_020630::12::fbp20 | GACCTTGGAGAACAGTCAGGAGGATCCAAAGTGGGAATTCCCTCGGAAGAA<br>CTTGGTTCTTGGAAAAACTCTAGGAGAAGGCGAATTTGGAAAAGTGGTCAA<br>GGCAACGGCCTTCCATCT<br>(SEQ ID NO: 54) |
| PAX8::NM003466::9-<br>PPARG::NM_005037::2::fbp20 | GGCCAGGCCCTCCTCTCAGAAATGACCATGGTTGACACAGAGATGCCATTC<br>TGGCCCACCAACTTTGGGATCAGCTCCGTGGATCTCTCCGTAATGGAAGAC<br>CACTCCCACTCCTTTGAT<br>(SEQ ID NO: 16) |
| SLC34A2::NM_006424::4-<br>ROS1::NM_002944::34::fbp20 | GCCTTCCAGCTGGTTGGAGATGATTTTTGGATACCAGAAACAAGTTTCATA<br>CTTACTATTATAGTTGGAATATTTCTGGTTGTTACAATCCCACTGACCTTT<br>GTCTGGCATAGAAGATTA<br>(SEQ ID NO: 55) |
| SLC45A3::NM_033102::1-<br>BRAF::NM_004333::8::fbp20 | AGCCGCGCGCCTCGGCCAGGCCCCAAATTCTCACCAGTCCGTCTCCTTCAA<br>AATCCATTCCAATTCCACAGCCCTTCCGACCAGCAGATGAAGATCATCGAA<br>ATCAATTTGGGCAACGAG<br>(SEQ ID NO: 56) |
| CD74::NM_004355::6-<br>ROS1::NM_002944::34::fbp30 | GCAAAAGCCCACTGACGCTCCACCGAAAGATGATTTTTGGATACCAGAAAC<br>AAGTTTCATACTTACTATTATAGTTGGAATATTTCTGGTTGTTACAATCCC<br>ACTGACCTTTGTCTGGCA<br>(SEQ ID NO: 57) |
| EML4::NM_019063::13-<br>ALK::NM_004304::20::fbp30 | AGAGCCCACACCTGGGAAAGGACCTAAAGTGTACCGCCGGAAGCACCAGGA<br>GCTGCAAGCCATGCAGATGGAGCTGCAGAGCCCTGAGTACAAGCTGAGCAA<br>GCTCCGCACCTCGACCAT<br>(SEQ ID NO: 58) |
| ETV6::NM_001987::5-<br>NTRK3:NM_002530::15::fbp30 | GCACGCCATGCCCATTGGGAGAATAGCAGATGTGCAGCACATTAAGAGGAG<br>AGACATCGTGCTGAAGCGAGAACTGGGTGAGGGAGCCTTTGGAAAGGTCTT<br>CCTGGCCGAGTGCTACAA<br>(SEQ ID NO: 59) |
| FGFR3::NM_000142::17-<br>TACC3::NM_006342::11::fbp30 | GAGTGCTGGCATGCCGCGCCCTCCCAGAGGCCCACCTTCAAGCAGCTGGTG<br>GAGGACCTGGACCGTGTCCTTACCGTGACGTCCACCGACGTAAAGGCGACA<br>CAGGAGGAGAACCGGGAG<br>(SEQ ID NO: 8) |
| LMNA::NM_005572::2-<br>NTRK1::NM_002529::11::fbp30 | TGCATGAT CTGCGGGGCCAGGTGGCCAAGGTCTCGGTGGCTGTGGGCCTG<br>GCCGTCTTTGCCTGCCTCTTCCTTTCTACGCTGCTCCTTGTGCTCAACAAA<br>TGTGGACGGAGAAACAAGT<br>(SEQ ID NO: 60) |
| TPM3::NM_152263::8-<br>NTRK1::NM_002529::10::fbp30 | GCTGGAAAAGACAATTGATGACCTGGAAGACACTAACAGCACATCTGGAGA<br>CCCGGTGGAGAAGAAGGACGAAACACCTTTTGGGGTCTCGGTGGCTGTGGG<br>CCTGGCCGTCTTTGCCTG<br>(SEQ ID NO: 61) |
| FGFR3::NM_000142::17-<br>BAW2L1::NM_018842::2::fbp30 | GAGTGCTGGCATGCCGCGCCCTCCCAGAGGCCCACCTTCAAGCAGCTGGTG<br>GAGGACCTGGACCGTGTCCTTACCGTGACGTCCACCGACAATGTTATGGAA<br>CAGTTCAATCCTGGGCTG<br>(SEQ ID NO: 62) |
| KIF5B::NM_004521::24-<br>RET:NM_020630::11::fbp30 | GGCCAGAAGAGGGCATTCTGCACAGATTGATCCACTGTGCGACGAGCTGTG<br>CCGCACGGTGATCGCAGCCGCTGTCCTCTTCTCCTTCATCGTCTCGGTGCT<br>GCTGTCTGCCTTCTGCAT<br>(SEQ ID NO: 63) |
| NCOA4::NM_005437::7-<br>RET::NM_020630::12::fbp30 | CCCAAAAGCAGACCTTGGAGAACAGTCAGGAGGATCCAAAGTGGGAATTCC<br>CTCGGAAGAACTTGGTTCTTGGAAAAACTCTAGGAGAAGGCGAATTTGGAA<br>AAGTGGTCAAGGCAACGG<br>(SEQ ID NO: 64) |
| PAX8::NM__003466::9-<br>PPARG::NM_005037::2::fbp30 | GCAGTTCACGGGCCAGGCCCTCCTCTCAGAAATGACCATGGTTGACACAGA<br>GATGCCATTCTGGCCCACCAACTTTGGGATCAGCTCCGTGGATCTCTCCGT<br>AATGGAAGACCACTCCCA<br>(SEQ ID NO: 17) |

| Probe name | probe sequence |
| --- | --- |
| SLC34A2::NM_006424::4-ROS1::NM_002944::34::fbp30 | TCTTAGTAGCGCCTTCCAGCTGGTTGGAGATGATTTTTGGATACCAGAAAC<br>AAGTTTCATACTTACTATTATAGTTGGAATATTTCTGGTTGTTACAATCCC<br>ACTGACCTTTGTCTGGCA<br>(SEQ ID NO: 65) |
| SLC45A3::NM_033102::1-BRAF::NM_004333::8::fbp30 | TCCGGGTGACAGCCGCGCGCCTCGGCCAGGCCCCAAATTCTCACCAGTCCG<br>TCTCCTTCAAAATCCATTCCAATTCCACAGCCCTTCCGACCAGCAGATGAA<br>GATCATCGAAATCAATTT<br>(SEQ ID NO: 66) |
| CD74::NM_004355::6-ROS1::NM_002944::34::fbp40 | ACTCCTTGGAGCAAAAGCCCACTGACGCTCCACCGAAAGATGATTTTTGGA<br>TACCAGAAACAAGTTTCATACTTACTATTATAGTTGGAATATTTCTGGTTG<br>TTACAATCCCACTGACCT<br>(SEQ ID NO: 67) |
| EML4::NM_019063::13-ALK::NM_004304::20::fbp40 | AAACTACTGTAGAGCCCACACCTGGGAAAGGACCTAAAGTGTACCGCCGGA<br>AGCACCAGGAGCTGCAAGCCATGCAGATGGAGCTGCAGAGCCCTGAGTACA<br>AGCTGAGCAAGCTCCGCA<br>(SEQ ID NO: 68) |
| ETV6::NM_001987::5-NTRK3::NM_002530::15::fbp40 | CGCCTGAAGAGCACGCCATGCCCATTGGGAGAATAGCAGATGTGCAGCACA<br>TTAAGAGGAGAGACATCGTGCTGAAGCGAGAACTGGGTGAGGGAGCCTTTG<br>GAAAGGTCTTCCTGGCCG<br>(SEQ ID NO: 69) |
| FGFR3::NM_000142::17-TACC3::NM_006342::11::fbp40 | ATGCCGCGCCCTCCCAGAGGCCCACCTTCAAGCAGCTGGTGGAGGACCTGG<br>ACCGTGTCCTTACCGTGACGTCCACCGACGTAAAGGCGACACAGGAGGAGA<br>ACCGGGAGCTGAGGAGCA<br>(SEQ ID NO: 9) |
| LMNA::NM_005572::2-NTRK1::NM_002529::11::fp40 | GAGGGCGAGCTGCATGATCTGCGGGGCCAGGTGGCCAAGGTCTCGGTGGCT<br>GTGGGCCTGGCCGTCTTTGCCTGCCTCTTCCTTTCTACGCTGCTCCTTGTG<br>CTCAACAAATGTGGACGG<br>(SEQ ID NO: 70) |
| TPM3::NM_152263::8-NTRK1::NM_002529::10::fbp40 | CGGTAGCCAAGCTGGAAAAGACAATTGATGACCTGGAAGACACTAACAGCA<br>CATCTGGAGACCCGGTGGAGAAGAAGGACGAAACACCTTTTGGGGTCTCGG<br>TGGCTGTGGGCCTGGCCG<br>(SEQ ID NO: 71) |
| FGFR3::NM_000142::17-BAIAP2L1::NM_018842::2::fbp40 | ATGCCGCGCCCTCCCAGAGGCCCACCTTCAAGCAGCTGGTGGAGGACCTGG<br>ACCGTGTCCTTACCGTGACGTCCACCGACAATGTTATGGAACAGTTCAATC<br>CTGGGCTGCGAAATTTAA<br>(SEQ ID NO: 72) |
| KIF5B::NM_004521::24-RET::NM_020630::11::fbp40 | CAAAGAATATGGCCAGAAGAGGGCATTCTGCACAGATTGATCCACTGTGCG<br>ACGAGCTGTGCCGCACGGTGATCGCAGCCGCTGTCCTCTTCTCCTTCATCG<br>TCTCGGTGCTGCTGTCTG<br>(SEQ ID NO: 73) |
| NCOA4::NM_005437::7-RET::NM_020630::12::fbp40 | GACTGGCTTACCCAAAAGCAGACCTTGGAGAACAGTCAGGAGGATCCAAAG<br>TGGGAATTCCCTCGGAAGAACTTGGTTCTTGGAAAAACTCTAGGAGAAGGC<br>GAATTTGGAAAAGTGGTC<br>(SEQ ID NO: 74) |
| PAX8::NM_003466::9-PPARG::NM_005037::2::fbp40 | CCGTGTACGGGCAGTTCACGGGCCAGGCCCTCCTCTCAGAAATGACCATGG<br>TTGACACAGAGATGCCATTCTGGCCCACCAACTTTGGGATCAGCTCCGTGG<br>ATCTCTCCGTAATGGAAG<br>(SEQ ID NO: 18) |
| SLC34A2::NM_006424::4-ROS1::NM_002944::34::fbp40 | CCCTGGATATTCTTAGTAGCGCCTTCCAGCTGGTTGGAGATGATTTTTGGA<br>TACCAGAAACAAGTTTCATACTTACTATTATAGTTGGAATATTTCTGGTTG<br>TTACAATCCCACTGACCT<br>(SEQ ID NO: 75) |
| SLC45A3::NM_033102::1-BRAF::NM_004333::8::fbp40 | ACGCGCTGGCTCCGGGTGACAGCCGCGCGCCTCGGCCAGGCCCCAAATTCT<br>CACCAGTCCGTCTCCTTCAAAATCCATTCCAATTCCACAGCCCTTCCGACC<br>AGCAGATGAAGATCATCG<br>(SEQ ID NO 76) |
| CD74::NM_004355::6-ROS1::NM_002944::34::fbp50 | ATGAGCAGGCACTCCTTGGAGCAAAAGCCCACTGACGCTCCACCGAAAGAT<br>GATTTTTGGATACCAGAAACAAGTTTCATACTTACTATTATAGTTGGAATA<br>TTTCTGGTTGTTACAATC<br>(SEQ ID NO: 27) |

-continued

| Probe name | probe sequence |
|---|---|
| EML4::NM_019063::13-ALK::NM_004304::20::fbp50 | ATATGGAGCAAAACTACTGTAGAGCCCACACCTGGGAAAGGACCTAAAGTG<br>TACCGCCGGAAGCACCAGGAGCTGCAAGCCATGCAGATGGAGCTGCAGAGC<br>CCTGAGTACAAGCTGAGC<br>(SEQ ID NO: 28) |
| ETV6::NM_001987::5-NTRK3::NM_002530::15::fbp50 | TCTGTCTCCCCGCCTGAAGAGCACGCCATGCCCATTGGGAGAATAGCAGAT<br>GTGCAGCACATTAAGAGGAGAGACATCGTGCTGAAGCGAGAACTGGGTGAG<br>GGAGCCTTTGGAAAGGTC<br>(SEQ ID NO: 29) |
| FGFR3::NM_000142::17-TACC3::NM_006342::11::fbp50 | CTCCCAGAGGCCCACCTTCAAGCAGCTGGTGGAGGACCTGGACCGTGTCCT<br>TACCGTGACGTCCACCGACGTAAAGGCGACACAGGAGGAGAACCGGGAGCT<br>GAGGAGCAGGTGTGAGGA<br>(SEQ ID NO: 5) |
| LMNA::NM_005572::2-NTRK1::NM_002529::11::fp50 | GCGCACGCTGGAGGGCGAGCTGCATGATCTGCGGGGCCAGGTGGCCAAGGT<br>CTCGGTGGCTGTGGGCCTGGCCGTCTTTGCCTGCCTCTTCCTTTCTACGCT<br>GCTCCTTGTGCTCAACAA<br>(SEQ ID NO: 30) |
| TPM3::NM_152263::8-NTRK1::NM_002529::10::fbp50 | AGATAAATATGAGGAAGAAATCAAGATTCTTACTGATAAACTCAAGGAGAC<br>ACTAACAGCACATCTGGAGACCCGGTGGAGAAGAAGGACGAAACACCTTTT<br>GGGGTCTCGGTGGCTGTG<br>(SEQ ID NO: 31) |
| FGFR3::NM_000142::17-BAIAP2L1::NM_018842::2::fbp50 | CTCCCAGAGGCCCACCTTCAAGCAGCTGGTGGAGGACCTGGACCGTGTCCT<br>TACCGTGACGTCCACCGACAATGTTATGGAACAGTTCAATCCTGGGCTGCG<br>AAATTTAATAAACCTGGG<br>(SEQ ID NO: 32) |
| KIF5B::NM_004521::24-RET::NM_020630::11::fbp50 | GCAGTCAGGTCAAAGAATATGGCCAGAAGAGGGCATTCTGCACAGATTGAT<br>CCACTGTGCGACGAGCTGTGCCGCACGGTGATCGCAGCCGCTGTCCTCTTC<br>TCCTTCATCGTCTCGGTG<br>(SEQ ID NO: 33) |
| NCOA4::NM_005437::7-RET::NM_020630::12::fbp50 | CGACCCCCAGGACTGGCTTACCCAAAAGCAGACCTTGGAGAACAGTCAGGA<br>GGATCCAAAGTGGGAATTCCCTCGGAAGAACTTGGTTCTTGGAAAAACTCT<br>AGGAGAAGGCGAATTTGG<br>(SEQ ID NO: 34) |
| PAX8::NM_003466::9-PPARG::NM_005037::2::fbp50 | CATGCTGCCTCCGTGTACGGGCAGTTCACGGGCCAGGCCCTCCTCTCAGAA<br>ATGACCATGGTTGACACAGAGATGCCATTCTGGCCCACCAACTTTGGGATC<br>AGCTCCGTGGATCTCTCC<br>(SEQ ID NO 14) |
| SLC34A2::NM_006424::4-ROS1::NM_002944::34::fbp50 | TTCGTGTGCTCCCTGGATATTCTTAGTAGCGCCTTCCAGCTGGTTGGAGAT<br>GATTTTTGGATACCAGAAACAAGTTTCATACTTACTATTATAGTTGGAATA<br>TTTCTGGTTGTTACAATC<br>(SEQ ID NO: 35) |
| SLC45A3::NM_033102::1-BRAF::NM_004333::8::fbp50 | ACCAGCCTGCACGCGCTGGCTCCGGGTGACAGCCGCGCGCCTCGGCCAGGC<br>CCCAAATTCTCACCAGTCCGTCTCCTTCAAAATCCATTCCAATTCCACAGC<br>CCTTCCGACCAGCAGATG<br>(SEQ ID NO: 36) |

It is noted that universal probes for FGFR3-TACC3 (0 bp) and FGFR3-BAIAP2L1 (0 bp) have the same sequence of SEQ ID NO: 4. The universal probes for CD74-ROS1 (0 bp) and SLC34A2-ROS1 (0 bp) have the same sequence of SEQ ID NO: 19.

The results show that 0 bp probes, 0+50 bp and mix of probes capture similar or higher number of fusion fragments, depending on the fusion in question (FIG. 4).

The probe mix/design described in this invention, hence, provide effective capture of fusion molecules, enriching for desired specific fusions while optimizing the reads coming from mutant form when compared to untargeted WT forms of genes.

What is claimed is:

1. A probe set comprising:
   at least one probe comprising:
   a first portion of the probe complementary to a primary nucleotide portion of a target nucleic acid, and
   a second portion of the probe complementary to a secondary nucleotide portion of the target nucleic acid,
   wherein the probe overlaps a breakpoint between the primary and the secondary nucleotide portion of the target nucleic acid, and
   wherein the length of second portion of the probe represents about 9% to about 42% of a total probe length, and
   at least one further probe complementary only to the primary nucleotide portion of the target nucleic acid, wherein the further probe does not overlap a breakpoint between the primary and the secondary nucleotide portion of the target nucleic acid.

2. The probe set of claim 1, wherein the primary nucleotide portion of the target nucleic acid is selected from the group consisting of: a fusion gene, a transcript encoding primary fusion partner, or an exon skipping transcript encoding one exon, and
   wherein the second portion of the probe complementary to the secondary nucleotide portion of the target nucleic acid is selected from the group consisting of: a fusion gene, a transcript encoding secondary fusion partner, or an exon skipping transcript encoding secondary exon.

3. The probe set of claim 1, wherein the length of the second portion of the probe represents a segment of the total length, the segment of the total length selected from the group consisting of: 9%, 17%, 25%, 33% or 42% of a total probe length.

4. The probe set of claim 1, wherein the primary nucleotide portion of the target nucleic acid is the primary fusion partner that is a kinase molecule, and the secondary nucleotide portion of the target nucleic acid is the secondary fusion partner that is a non-kinase molecule.

5. The probe set of claim 1, wherein the probe set is included within a kit.

6. The probe set of claim 1, wherein the probe set is contained within a composition.

7. A probe comprising:
   a first portion of the probe complementary to a primary nucleotide portion of a target nucleic acid that is selected from the group consisting of:
   a fusion gene or transcript encoding primary fusion partner, or
   an exon skipping transcript encoding one exon, and
   a second portion of the probe complementary to a secondary nucleotide portion of the target nucleic acid that is selected from the group consisting of:
   a fusion gene or transcript encoding a secondary fusion partner, or
   an exon skipping transcript encoding secondary exon, and
   wherein the probe overlaps a breakpoint between the primary and the secondary nucleotide portion of the target nucleic acid, and
   wherein the length of second portion of the probe is 10 to 50 base pair (bp) long and a total probe length is 120 bp.

8. The probe of claim 7, wherein the length of the second portion of the probe has 10, 20, 30, 40, or 50 bp.

* * * * *

SEQUENCE LISTING

<160> NUMBER OF SEQ ID NOS: 76

<210> SEQ ID NO 1
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
gaccgtgtcc ttaccgtgac gtccaccgac gtaaaggcga cacaggagga gaaccgggag    60
ctgaggagca ggtgtgagga gctccacggg aagaacctgg aactggggaa gatcatggac   120

<210> SEQ ID NO 2
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
cccaccttca agcagctggt ggaggacctg gaccgtgtcc ttaccgtgac gtccaccgac    60
gtaaaggcga cacaggagga gaaccgggag ctgaggagca ggtgtgagga gctccacggg   120

<210> SEQ ID NO 3
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gagtgctggc atgccgcgcc ctcccagagg cccaccttca agcagctggt ggaggacctg    60
gaccgtgtcc ttaccgtgac gtccaccgac gtaaaggcga cacaggagga gaaccgggag   120

<210> SEQ ID NO 4
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tgcacacacg acctgtacat gatcatgcgg gagtgctggc atgccgcgcc ctcccagagg    60
cccaccttca agcagctggt ggaggacctg gaccgtgtcc ttaccgtgac gtccaccgac   120

<210> SEQ ID NO 5
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ctcccagagg cccaccttca agcagctggt ggaggacctg gaccgtgtcc ttaccgtgac    60
gtccaccgac gtaaaggcga cacaggagga gaaccgggag ctgaggagca ggtgtgagga   120

<210> SEQ ID NO 6

```
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
acctgtacat gatcatgcgg gagtgctggc atgccgcgcc ctcccagagg cccaccttca    60
agcagctggt ggaggacctg gaccgtgtcc ttaccgtgac gtccaccgac gtaaaggcga   120

<210> SEQ ID NO 7
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gatcatgcgg gagtgctggc atgccgcgcc ctcccagagg cccaccttca agcagctggt    60
ggaggacctg gaccgtgtcc ttaccgtgac gtccaccgac gtaaaggcga cacaggagga   120

<210> SEQ ID NO 8
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gagtgctggc atgccgcgcc ctcccagagg cccaccttca agcagctggt ggaggacctg    60
gaccgtgtcc ttaccgtgac gtccaccgac gtaaaggcga cacaggagga gaaccgggag   120

<210> SEQ ID NO 9
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
atgccgcgcc ctcccagagg cccaccttca agcagctggt ggaggacctg gaccgtgtcc    60
ttaccgtgac gtccaccgac gtaaaggcga cacaggagga gaaccgggag ctgaggagca   120

<210> SEQ ID NO 10
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ggcagttcac gggccaggcc ctcctctcag aaatgaccat ggttgacaca gagatgccat    60
tctggcccac caactttggg atcagctccg tggatctctc cgtaatggaa gaccactccc   120

<210> SEQ ID NO 11
<211> LENGTH: 120
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 11
atgcctttcc ccatgctgcc tccgtgtacg ggcagttcac gggccaggcc ctcctctcag      60
aaatgaccat ggttgacaca gagatgccat tctggcccac caactttggg atcagctccg    120

<210> SEQ ID NO 12
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
agcaagtcgg ctccggggtc ccgcccttca atgcctttcc ccatgctgcc tccgtgtacg      60
ggcagttcac gggccaggcc ctcctctcag aaatgaccat ggttgacaca gagatgccat    120

<210> SEQ ID NO 13
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
aaatgaccat ggttgacaca gagatgccat tctggcccac caactttggg atcagctccg      60
tggatctctc cgtaatggaa gaccactccc actcctttga tatcaagccc ttcactactg    120

<210> SEQ ID NO 14
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
catgctgcct ccgtgtacgg gcagttcacg ggccaggccc tcctctcaga aatgaccatg      60
gttgacacag agatgccatt ctggcccacc aactttggga tcagctccgt ggatctctcc    120

<210> SEQ ID NO 15
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tcctctcaga aatgaccatg gttgacacag agatgccatt ctggcccacc aactttggga      60
tcagctccgt ggatctctcc gtaatggaag accactccca ctcctttgat atcaagccct    120

<210> SEQ ID NO 16
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
ggccaggccc tcctctcaga aatgaccatg gttgacacag agatgccatt ctggcccacc    60
aactttggga tcagctccgt ggatctctcc gtaatggaag accactccca ctcctttgat   120

<210> SEQ ID NO 17
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
gcagttcacg ggccaggccc tcctctcaga aatgaccatg gttgacacag agatgccatt    60
ctggcccacc aactttggga tcagctccgt ggatctctcc gtaatggaag accactccca   120

<210> SEQ ID NO 18
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ccgtgtacgg gcagttcacg ggccaggccc tcctctcaga aatgaccatg gttgacacag    60
agatgccatt ctggcccacc aactttggga tcagctccgt ggatctctcc gtaatggaag   120

<210> SEQ ID NO 19
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19 atgattttg gataccagaa acaagtttca tacttactat tatagttgga atatttctgg    60
ttgttacaat cccactgacc tttgtctggc atagaagatt aaagaatcaa aaaagtgcca   120

<210> SEQ ID NO 20
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
tgtaccgccg gaagcaccag gagctgcaag ccatgcagat ggagctgcag agccctgagt    60
acaagctgag caagctccgc acctcgacca tcatgaccga ctacaacccc aactactgct   120

<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
atgtgcagca cattaagagg agagacatcg tgctgaagcg agaactgggt gagggagcct    60
ttggaaaggt cttcctggcc gagtgctaca acctcagccc gaccaaggac aagatgcttg   120

<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gtctcggtgg ctgtgggcct ggccgtcttt gcctgcctct tcctttctac gctgctcctt       60
gtgctcaaca aatgtggacg gagaaacaag tttgggatca accgcccggc tgtgctggct      120

<210> SEQ ID NO 23
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
acactaacag cacatctgga gacccggtgg agaagaagga cgaaacacct tttggggtct       60
cggtggctgt gggcctggcc gtctttgcct gcctcttcct ttctacgctg ctccttgtgc      120

<210> SEQ ID NO 24
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
atccactgtg cgacgagctg tgccgcacgg tgatcgcagc cgctgtcctc ttctccttca       60
tcgtctcggt gctgctgtct gccttctgca tccactgcta ccacaagttt gcccacaagc      120

<210> SEQ ID NO 25
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gaggatccaa agtgggaatt ccctcggaag aacttggttc ttggaaaaac tctaggagaa       60
ggcgaatttg gaaaagtggt caaggcaacg gccttccatc tgaaaggcag agcagggtac      120

<210> SEQ ID NO 26
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gccccaaatt ctcaccagtc cgtctccttc aaaatccatt ccaattccac agcccttccg       60
accagcagat gaagatcatc gaaatcaatt tgggcaacga accgatcct catcagctcc       120

<210> SEQ ID NO 27
<211> LENGTH: 120

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
atgagcaggc actccttgga gcaaaagccc actgacgctc caccgaaaga tgattttgg      60 ataccagaaa caagtttcat acttactatt atagttggaa tatttctggt tgttacaatc    120

<210> SEQ ID NO 28
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
atatggagca aaactactgt agagcccaca cctgggaaag gacctaaagt gtaccgccgg     60
aagcaccagg agctgcaagc catgcagatg gagctgcaga gccctgagta caagctgagc    120

<210> SEQ ID NO 29
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
tctgtctccc cgcctgaaga gcacgccatg cccattggga gaatagcaga tgtgcagcac    60
attaagagga gagacatcgt gctgaagcga gaactgggtg agggagcctt tggaaaggtc    120

<210> SEQ ID NO 30
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
gcgcacgctg gagggcgagc tgcatgatct gcggggccag gtggccaagg tctcggtggc    60
tgtgggcctg gccgtctttg cctgcctctt cctttctacg ctgctccttg tgctcaacaa    120

<210> SEQ ID NO 31
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
agataaatat gaggaagaaa tcaagattct tactgataaa ctcaaggaga cactaacagc    60
acatctggag acccggtgga gaagaaggac gaaacacctt tgggggtctc ggtggctgtg    120

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 32
ctcccagagg cccaccttca agcagctggt ggaggacctg gaccgtgtcc ttaccgtgac    60
gtccaccgac aatgttatgg aacagttcaa tcctgggctg cgaaatttaa taaacctggg  120

<210> SEQ ID NO 33
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
gcagtcaggt caaagaatat ggccagaaga gggcattctg cacagattga tccactgtgc    60
gacgagctgt gccgcacggt gatcgcagcc gctgtcctct tctccttcat cgtctcggtg  120

<210> SEQ ID NO 34
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34 cgaccccag gactggctta cccaaaagca gaccttggag aacagtcagg aggatccaaa     60
gtgggaattc cctcggaaga acttggttct tggaaaaact ctaggagaag gcgaatttgg  120

<210> SEQ ID NO 35
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ttcgtgtgct ccctggatat tcttagtagc gccttccagc tggttggaga tgattttgg     60 ataccagaaa caagtttcat acttactatt atagttggaa tatttctggt tgttacaatc  120

<210> SEQ ID NO 36
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
accagcctgc acgcgctggc tccgggtgac agccgcgcgc ctcggccagg ccccaaattc    60
tcaccagtcc gtctccttca aaatccattc caattccaca gcccttccga ccagcagatg  120

<210> SEQ ID NO 37
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
caccgaaaga tgattttttgg ataccagaaa caagtttcat acttactatt atagttggaa    60
tatttctggt tgttacaatc ccactgacct ttgtctggca tagaagatta aagaatcaaa    120

<210> SEQ ID NO 38
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
gacctaaagt gtaccgccgg aagcaccagg agctgcaagc catgcagatg gagctgcaga    60
gccctgagta caagctgagc aagctccgca cctcgaccat catgaccgac tacaacccca    120

<210> SEQ ID NO 39
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gaatagcaga tgtgcagcac attaagagga gagacatcgt gctgaagcga gaactgggtg    60
agggagcctt tggaaaggtc ttcctggccg agtgctacaa cctcagcccg accaaggaca    120

<210> SEQ ID NO 40
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
gtggccaagg tctcggtggc tgtgggcctg gccgtctttg cctgcctctt cctttctacg    60
ctgctccttg tgctcaacaa atgtggacgg agaaacaagt ttgggatcaa ccgcccggct    120

<210> SEQ ID NO 41
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
acctggaaga cactaacagc acatctggag acccggtgga gaagaaggac gaaacacctt    60
ttggggtctc ggtggctgtg ggcctggccg tctttgcctg cctcttcctt tctacgctgc    120

<210> SEQ ID NO 42
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
acctgtacat gatcatgcgg gagtgctggc atgccgcgcc ctcccagagg cccaccttca    60
agcagctggt ggaggacctg gaccgtgtcc ttaccgtgac gtccaccgac aatgttatgg    120

<210> SEQ ID NO 43
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
cacagattga tccactgtgc gacgagctgt gccgcacggt gatcgcagcc gctgtcctct      60
tctccttcat cgtctcggtg ctgctgtctg ccttctgcat ccactgctac cacaagtttg     120

<210> SEQ ID NO 44
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
aacagtcagg aggatccaaa gtgggaattc cctcggaaga acttggttct tggaaaaact      60
ctaggagaag gcgaatttgg aaaagtggtc aaggcaacgg ccttccatct gaaaggcaga     120

<210> SEQ ID NO 45
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
tggttggaga tgattttttgg ataccagaaa caagtttcat acttactatt atagttggaa     60
tatttctggt tgttacaatc ccactgacct tgtctggca tagaagatta aagaatcaaa      120

<210> SEQ ID NO 46
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
ctcggccagg ccccaaattc tcaccagtcc gtctccttca aaatccattc caattccaca      60
gcccttccga ccagcagatg aagatcatcg aaatcaattt gggcaacgag accgatcctc     120

<210> SEQ ID NO 47
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
actgacgctc caccgaaaga tgattttttgg ataccagaaa caagtttcat acttactatt    60
atagttggaa tatttctggt tgttacaatc ccactgacct tgtctggca tagaagatta     120

<210> SEQ ID NO 48
<211> LENGTH: 120
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 48
cctgggaaag gacctaaagt gtaccgccgg aagcaccagg agctgcaagc catgcagatg    60
gagctgcaga gccctgagta caagctgagc aagctccgca cctcgaccat catgaccgac   120

<210> SEQ ID NO 49
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
cccattggga gaatagcaga tgtgcagcac attaagagga gagacatcgt gctgaagcga    60
gaactgggtg agggagcctt tggaaaggtc ttcctggccg agtgctacaa cctcagcccg   120

<210> SEQ ID NO 50
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
gcggggccag gtggccaagg tctcggtggc tgtgggcctg gccgtctttg cctgcctctt    60
cctttctacg ctgctccttg tgctcaacaa atgtggacgg agaaacaagt ttgggatcaa   120

<210> SEQ ID NO 51
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
acaattgatg acctggaaga cactaacagc acatctggag acccggtgga gaagaaggac    60
gaaacacctt ttggggtctc ggtggctgtg ggcctggccg tctttgcctg cctcttcctt   120

<210> SEQ ID NO 52
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
gatcatgcgg gagtgctggc atgccgcgcc ctcccagagg cccaccttca agcagctggt    60
ggaggacctg gaccgtgtcc ttaccgtgac gtccaccgac aatgttatgg aacagttcaa   120

<210> SEQ ID NO 53
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
gggcattctg cacagattga tccactgtgc gacgagctgt gccgcacggt gatcgcagcc    60
gctgtcctct tctccttcat cgtctcggtg ctgctgtctg ccttctgcat ccactgctac   120

<210> SEQ ID NO 54
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gaccttggag aacagtcagg aggatccaaa gtgggaattc cctcggaaga acttggttct    60
tggaaaaact ctaggagaag gcgaatttgg aaaagtggtc aaggcaacgg ccttccatct   120

<210> SEQ ID NO 55
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
gccttccagc tggttggaga tgattttggg ataccagaaa caagtttcat acttactatt    60
atagttggaa tatttctggt tgttacaatc ccactgacct tgtctggca tagaagatta   120

<210> SEQ ID NO 56
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
agccgcgcgc ctcggccagg ccccaaattc tcaccagtcc gtctccttca aaatccattc    60
caattccaca gcccttccga ccagcagatg aagatcatcg aaatcaattt gggcaacgag   120

<210> SEQ ID NO 57
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
gcaaaagccc actgacgctc caccgaaaga tgattttggg ataccagaaa caagtttcat    60
acttactatt atagttggaa tatttctggt tgttacaatc ccactgacct tgtctggca   120

<210> SEQ ID NO 58
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
agagcccaca cctgggaaag gacctaaagt gtaccgccgg aagcaccagg agctgcaagc    60
catgcagatg gagctgcaga gccctgagta caagctgagc aagctccgca cctcgaccat    120

<210> SEQ ID NO 59
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
gcacgccatg cccattggga gaatagcaga tgtgcagcac attaagagga gagacatcgt    60
gctgaagcga gaactgggtg agggagcctt tggaaaggtc ttcctggccg agtgctacaa    120

<210> SEQ ID NO 60
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
tgcatgatct gcggggccag gtggccaagg tctcggtggc tgtgggcctg gccgtctttg    60
cctgcctctt cctttctacg ctgctccttg tgctcaacaa atgtggacgg agaaacaagt    120

<210> SEQ ID NO 61
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
gctggaaaag acaattgatg acctggaaga cactaacagc acatctggag acccggtgga    60
gaagaaggac gaaacacctt tggggtctc ggtggctgtg ggcctggccg tctttgcctg    120

<210> SEQ ID NO 62
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
gagtgctggc atgccgcgcc ctcccagagg cccaccttca agcagctggt ggaggacctg    60
gaccgtgtcc ttaccgtgac gtccaccgac aatgttatgg aacagttcaa tcctgggctg    120

<210> SEQ ID NO 63
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
ggccagaaga gggcattctg cacagattga tccactgtgc gacgagctgt gccgcacggt    60
gatcgcagcc gctgtcctct tctccttcat cgtctcggtg ctgctgtctg ccttctgcat    120

<210> SEQ ID NO 64
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
cccaaaagca gaccttggag aacagtcagg aggatccaaa gtgggaattc cctcggaaga      60
acttggttct tggaaaaact ctaggagaag gcgaatttgg aaaagtggtc aaggcaacgg     120

<210> SEQ ID NO 65
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
tcttagtagc gccttccagc tggttggaga tgattttgg ataccagaaa caagtttcat       60
acttactatt atagttggaa tatttctggt tgttacaatc ccactgacct ttgtctggca     120

<210> SEQ ID NO 66
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
tccgggtgac agccgcgcgc ctcggccagg ccccaaattc tcaccagtcc gtctccttca      60
aaatccattc caattccaca gcccttccga ccagcagatg aagatcatcg aaatcaattt     120

<210> SEQ ID NO 67
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
actccttgga gcaaaagccc actgacgctc caccgaaaga tgattttgg ataccagaaa       60 caagtttcat acttactatt atagttggaa tatttctggt tgttacaatc ccactgacct    120

<210> SEQ ID NO 68
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
aaactactgt agagcccaca cctgggaaag gacctaaagt gtaccgccgg aagcaccagg      60
agctgcaagc catgcagatg gagctgcaga gccctgagta caagctgagc aagctccgca    120

<210> SEQ ID NO 69
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
cgcctgaaga gcacgccatg cccattggga gaatagcaga tgtgcagcac attaagagga    60
gagacatcgt gctgaagcga gaactgggtg agggagcctt tggaaaggtc ttcctggccg   120

<210> SEQ ID NO 70
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
gagggcgagc tgcatgatct gcggggccag gtggccaagg tctcggtggc tgtgggcctg    60
gccgtctttg cctgcctctt cctttctacg ctgctccttg tgctcaacaa atgtggacgg   120

<210> SEQ ID NO 71
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
cggtagccaa gctggaaaag acaattgatg acctggaaga cactaacagc acatctggag    60
acccggtgga gaagaaggac gaaacacctt ttggggtctc ggtggctgtg ggcctggccg   120

<210> SEQ ID NO 72
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
atgccgcgcc ctcccagagg cccaccttca agcagctggt ggaggacctg gaccgtgtcc    60
ttaccgtgac gtccaccgac aatgttatgg aacagttcaa tcctgggctg cgaaatttaa   120

<210> SEQ ID NO 73
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
caaagaatat ggccagaaga gggcattctg cacagattga tccactgtgc gacgagctgt    60
gccgcacggt gatcgcagcc gctgtcctct tctccttcat cgtctcggtg ctgctgtctg   120

<210> SEQ ID NO 74
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 74
gactggctta cccaaaagca gaccttggag aacagtcagg aggatccaaa gtgggaattc    60
cctcggaaga acttggttct tggaaaaact ctaggagaag gcgaatttgg aaaagtggtc   120

<210> SEQ ID NO 75
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
ccctggatat tcttagtagc gccttccagc tggttggaga tgatttttgg ataccagaaa    60
caagtttcat acttactatt atagttggaa tatttctggt tgttacaatc ccactgacct   120

<210> SEQ ID NO 76
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
acgcgctggc tccgggtgac agccgcgcgc ctcggccagg ccccaaattc tcaccagtcc    60
gtctccttca aaatccattc caattccaca gcccttccga ccagcagatg aagatcatcg   120
```